United States Patent [19]

Holland et al.

[11] Patent Number: 5,550,050

[45] Date of Patent: Aug. 27, 1996

[54] METHOD FOR IMPLANTING ENCAPSULATED CELLS IN A HOST

[75] Inventors: Laura M. Holland, Providence; Joseph P. Hammang; Seth A. Rudnick, both of Barrington; Michael J. Lysaght, E. Greenwich, all of R.I.; Keith E. Dionne, Rehoboth, Mass.

[73] Assignee: CytoTherapeutics, Inc., Providence, R.I.

[21] Appl. No.: 228,403

[22] Filed: Apr. 15, 1994

[51] Int. Cl.$^6$ ............................... C12N 5/00; C12N 1/38; C12N 1/36

[52] U.S. Cl. .................. 435/240.2; 435/240.72; 435/244; 435/245

[58] Field of Search ..................... 434/240.2, 240.22, 434/245, 244

[56] References Cited

U.S. PATENT DOCUMENTS

| | | | |
|---|---|---|---|
| 4,298,002 | 11/1981 | Ronel. | |
| 4,352,883 | 10/1982 | Lim | 435/178 |
| 4,409,331 | 11/1983 | Lim | 435/178 |
| 4,479,796 | 10/1984 | Kallok | 604/93 |
| 4,689,293 | 8/1987 | Goosen | 435/1 |
| 4,749,620 | 6/1988 | Rha | 428/402.2 |
| 4,789,550 | 12/1988 | Hommel | 424/493 |
| 4,806,355 | 2/1989 | Goosen | 424/424 |
| 4,892,538 | 1/1990 | Aebischer | 604/891.1 |
| 4,902,295 | 2/1990 | Walthall | 623/11 |
| 4,942,129 | 7/1990 | Goosen | 435/182 |
| 5,002,661 | 3/1991 | Chick | 210/192 |
| 5,026,365 | 6/1991 | Rossini | 604/891.1 |
| 5,084,350 | 1/1992 | Chang | 428/402.2 |
| 5,106,627 | 4/1992 | Aebischer | 424/424 |
| 5,182,111 | 1/1993 | Aebischer et al. | 424/424 |

FOREIGN PATENT DOCUMENTS

| | | |
|---|---|---|
| 78061 | 5/1983 | European Pat. Off.. |
| 127989 | 12/1984 | European Pat. Off.. |
| 147975 | 7/1985 | European Pat. Off.. |
| 188309 | 7/1986 | European Pat. Off.. |
| 301177 | 2/1989 | European Pat. Off.. |
| 387840 | 9/1990 | European Pat. Off.. |
| 2094833 | 9/1982 | United Kingdom. |
| WO91/09119 | 6/1991 | WIPO. |
| WO92/19195 | 10/1992 | WIPO. |
| WO93/22427 | 10/1993 | WIPO. |

OTHER PUBLICATIONS

Aebischer, Patrick, et al., "A Bioartificial Parathyroid," *Trans. Am. Soc. Artif. Intern. Organs*, 32, pp. 134–137 (1986).

Aebischer, P., et al., "Macroencapsulation of dopamine–secreting cells by coextrusion with an organic polymer solution," *Biomaterials*, 12, pp. 50–55 (1991).

Aebischer, Patrick, et al., "Long–Term Cross–Species Brain Transplantation of a Polymer–Encapsulated Dopamine–Secreting Cell Line," *Experimental Neurology*, 111, pp. 269–275 (1991).

Altman, J. J., et al., "Long–Term Plasma Glucose Normalization in Experimental Diabetic Rats With Macroencapsulated Implants of Benign Human Insulinomas," *Diabetes*, 35, pp. 625–633 (1986).

Bodziony, J., "Bioartificial endocrine pancreas: foreign–body reaction and effectiveness of diffusional transport of insulin and oxygen after long–term implantation of hollow fibers into rats," *Research in Experimental Medicine*, 192, pp. 305–316 (1992).

Cai, Zhuhui, et al., "Microencapsulated Hepatocytes for Bioartificial Liver Support," *Artificial Organs*, 12, pp. 388–393 (1988).

Christenson, Lisa, *Polymer Encapsulated Thymic Stromol Tissue: Biocompatibility, Procurement and Functional Studies*, Doctoral Dissertation, Division of Biology and Medicine, Brown University (May 1990).

Darquy, S., and Reach, G., "Immunoisolation of pancreatic B cells by microencapsulation," *Diabetologia*, 28, pp. 776–780 (1985).

Davalli, A. M., et al., "In Vitro Function of Adult Pig Islets: Effect of Culture in Different Media," *Transplantation Proceedings*, 24, pp. 2794–2795 (1992).

Dionne, Keith Evan, *Effect of Hypoxia on Insulin Secretion and Viability of Pancreatic Islet Tissue*, Doctoral Thesis, Department of Chemical Engineering, Massachusetts Institute of Technology (Dec. 8, 1989).

Dupuy, B., et al., "In situ polymerization of a microencapsulating medium round living cells," *Journal of Biomedical Materials Research*, 22, pp. 1061–1070 (1988).

Edmunds, W. W., et al., "Mass Transfer Effects in Microencapsulated Hybridoma Cells Producing Monoclonal Antibodies," *Applied Biochemistry and Biotechnology*, 20/21, pp. 603–619 (1989).

Enokido, Yasushi, and Hatanaka, Hiroshi, "High oxygen atmosphere for neuronal cell culture with nerve growth factor. II. Survival and growth of clonal rat pheochromocytoma PC12h cells," *Brain Research*, 536, pp. 23–29 (1990).

Fu, Xiao Wen, and Sun, Anthony M., "Microencapsulated Parathyroid Cells as a Bioartificial Parathyroid," *Transplantation*, 47, pp. 432–435 (1989).

Gage, Fred H., et al., "Experimental Approaches to Age–Related Cognitive Impairments," *Neurobiology of Aging*, 9, pp. 645–655 (1988).

Georgiou, H. M., and Mandel, T. E., "Islet Cell Subpopulations in Cultured Mouse Fetal Pancreas and Pancreatic Isografts," *Transplantation Proceedings*, 16, pp. 1055–1056 (1984).

(List continued on next page.)

*Primary Examiner*—John W. Rollins
*Attorney, Agent, or Firm*—Fish & Neave; Ivor R. Elrifi; Barbara A. Ruskin

[57] ABSTRACT

This invention provides methods for implanting encapsulated cells in a host comprising exposing cells to restrictive conditions for a sufficient period of time to establish a desired cell property in response to the restrictive conditions and implanting the encapsulated cells in a host, the cell property being substantially maintained following implantation. Also provided are cells produced by exposure to restrictive conditions.

13 Claims, 8 Drawing Sheets

OTHER PUBLICATIONS

Goldblatt, Harry, et al., "On the Malignant Transformation of Cells During Prolonged Culture Under Hypoxic Conditions in Vitro," *Biochemical Medicine*, 7, pp. 241–252 (1973).

Gupta, V., and Eberle, R., "Modulation of tumour cell colony growth in soft agar by oxygen and its mechanism," *Br. J. Cancer*, 49, pp. 587–593 (1984).

Holland, L. M., et al., "Effect of Reduced $pO_2$ on Viability & Function of Encapsulated Bovine Adrenal Chromaffin Cells," *ASAIO Abstracts*, p. 94 (1994).

Hong, A., et al., "Normobaric Oxygen as a Sensitizer of Hypoxic Tumor Cells," *Int. J. Radiation Oncology Biol. Phys.*, 16, pp. 1097–1099 (1989).

Iwata, Hiroo, et al., "Evaluation of Microencapsulated Islets in Agarose Gel as Bioartificial Pancreas by Studies of Hormone Secretion in Culture and Xenotransplantation," *Diabetes*, 38, pp. 224–225 (1989).

Jaeger, C. B., et al., "Growth of tumour cell lines in polymer capsules: ultrastructure of encapsulated PC12 cells," *Journal of Cytology*, 21, pp. 469–480 (1992).

Jaeger, C. B., et al., "Polymer encapsulated dopaminergic cell lines as 'alternative neural grafts,'" *Progress in Brain Research*, 82, pp. 41–46 (1990).

Jolley, W. B., et al., "Xenogeneic Pancreatic Islet Transplantation in Proteolytic Enzyme–Bonded Diffusion Chambers in Diabetic Rats," *Transplantation Proceedings*, 9, pp. 363–365 (1977).

Kallinowski, F., et al., "Growth–Related Changes of Oxygen Consumption Rates of Tumor Cells Grown In Vitro and In Vivo," *Journal of Cellular Physiology*, 138, pp. 183–191 (1989).

Lacy, Paul E., et al., "Transplantation of Insulin–Producing Tissue," *The American Journal of Medicine*, 70, pp. 589–594 (1981).

Lafferty, Kevin J., et al., "Thyroid Allograft Immunogenicity Is Reduced after a Period in Organ Culture," *Science*, 188, pp. 259–261 (1975).

Lavoie, Mark P., et al., "Two PC12 Pheochromocytoma Lines Sealed in Hollow Fiber–Based Capsules Tonically Release L–Dopa In Vitro," *Cell Transplantation*, 2, pp. 163–173 (1993).

Lentner, C., "Units of Measurement, Body Fluids, Composition of the Body, Nutrition," *Geigy Scientific Tables*, 1, pp. 165–175 (1981).

Lentner, C., "Physical Chemistry, Composition of Blood, Hematology, Somatometric Data," *Geigy Scientific Tables*, 3, pp. 71–163 (1984).

Leung, Yin F., et al., "Microencapsulation of Crystalline Insulin or Islets of Langerhans: An Insulin Diffusion Study," *Artificial Organs*, 7, pp. 208–212 (1983).

Livett, Bruce G., "Adrenal Medullary Chromaffin Cells in Vitro," *Physiological Reviews*, 64, pp. 1103–1161 (1984).

O'Shea, G. M., and Sun, A. M., "Prolonged Survival of Transplanted Islets of Langerhans Encapsulated in a Biocompatible Membrane," *Diabetes*, 35, pp. 943–946 (1986).

O'Shea, Geraldine M., et al., "Encapsulation of Rat Islets of Langerhans Prolongs Xenograft Survival in Diabetic Mice," *Biochimica et Biophysica Acta*, 804, pp. 133–136 (1984).

Pang, L. and Eyzaguirre, C., "Different effects of hypoxia on the membrane potential and input resistance of isolated and clustered carotid body glomus cells," *Brain Research*, 575, pp. 167–173 (1992).

Pollard, Jeffrey W., and Walker, John M., "Animal Cell Culture," *Methods in Molecular Biology*, 5, pp. 692–700 (1990).

Reach, G., "Bioartificial pancreas. Present state and future prospects," *Biomed. Biochim. Acta*, 43, pp. 569–576 (1984).

Rofstad, E. K., and Sutherland, R. M., "Growth and radiation sensitivity of the MLS human ovarian carcinoma cell line grown as multicellular spheroids and xenografted tumours," *Br. J. Cancer*, 59, pp. 28–35 (1989).

Spector, Reynold, and Johanson, Conrad E., "The Mammalian Choroid Plexus," *Scientific American*, pp. 68–74 (Nov. 1989).

Sugamori, M. E., and Sefton, M. V., "Microencapsulation of Pancreatic Islets in a Water Insoluble Polyacrylate," *Trans. Am. Soc. Artif. Intern. Organs*, 35, pp. 791–799 (1989).

Sun, Anthony M., et al., "Injectable Microencapsulated Islet Cells as a Bioartificial Pancreas," *Applied Biochemistry and Biotechnology*, 10, pp. 87–99 (1984).

Sun, Anthony M., et al., "The Use, in Diabetic Rats and Monkeys, of Artificial Capillary Units Containing Cultured Islets of Langerhans (Artificial Endocrine Pancreas)," *Diabetes*, 26, pp. 1136–1139 (1977).

Sun, Anthony M., et al., "Microencapsulated Hepatocytes as a Bioartificial Liver," *Trans. Am. Soc. Artif. Intern. Organs*, 32, pp. 39–41 (1986).

Sun, Anthony M., "Encapsulated Versus Modified Endocrine Cells for Organ Replacement," *Trans. Am. Soc. Artif. Intern. Organs*, 33, pp. 787–790 (1987).

Sun, A. M., et al., "Microencapsulated Hepatocytes: An In Vitro and In Vivo Study," *Biomat., Art. Cells, Art. Org.*, 15, pp. 483–496 (1987).

Sun, Anthony Mein-Fang, "Microencapsulated Cells as Hormone Delivery Systems," *CRC Critical Reviews in Therapeutic Drug Carrier Systems*, 4, pp. 1–12 (1987).

Talmage, David W., and Dart, Gladys A., "Effect of Oxygen Pressure During Culture on Survival of Mouse Thyroid Allografts," *Science*, 200, pp. 1066–1067 (1978).

Tze, W. J., et al., "Implantable Artificial Capillary Unit for Pancreatic Islet Allograft and Xenograft," *Diabetologia*, 16, pp. 247–252 (1979).

Wilson, David F., et al., "The Oxygen Dependence of Mitochondrial Oxidative Phosphorylation Measured by a New Optical Method for Measuring Oxygen Concentration," *The Journal of Biological Chemistry*, 263, pp. 2712–2718 (1988).

Wolffe, Alan P., and Tata, Jamshed R., "Primary culture, cellular stress and differentiated function," *FEBS Letters*, 176, pp. 8–13 (1984).

Young, S. D., and Hill, R. P., "Effects of Reoxygenation on Cells from Hypoxic Regions of Solid Tumors: Analysis of Transplanted Murine Tumors for Evidence of DNA Overreplication," *Cancer Research*, 50, pp. 5031–5038 (1990).

Aebischer, Patrick, et al., "Polymer Encapsulated PC12 Cells Transplanted in MPTP Lesioned Primates," *Soc. Neurosci. Abstr.* 16:963 (1990).

METHOD FOR IMPLANTING ENCAPSULATED CELLS IN A HOST

FIELD OF THE INVENTION

This invention relates to preparing encapsulated cells for implantation in a host by exposing the cells, either in vivo or in vitro, to one or more restrictive conditions that more closely match those at a desired implantation site for a sufficient period of time to establish a desired cell property in response to the restrictive condition.

BACKGROUND OF THE INVENTION

Encapsulated cells which produce a biologically active molecule, when implanted in a host, may be used to prevent or treat many diseases or disorders or to provide, restore or augment one or more metabolic functions in the host.

One approach to encapsulating cells is called "microencapsulation", wherein tiny spheres encapsulate a microscopic droplet of a cell-containing solution (Sefton et al., *Biotechnology and Bioengineering* 29, pp. 1135–1143 (1987); Sugamori et al., *Trans. Am. Soc. Artf. Intern. Organs* 35, pp. 791–799 (1989)).

Another approach to encapsulating cells, "macroencapsulation" involves encapsulating a plurality of cells in a thermoplastic capsule. Typically this is accomplished by loading cells into a hollow fiber and then sealing the extremities. Various types of macrocapsules are known in the art. In particular, Dionne et. al. (WO 92/19195) refers to a macrocapsule having cells dispersed in a matrix and a semipermeable surface jacket, and is incorporated herein by reference. See also Aebischer, U.S. Pat. Nos. 5,158,881, 5,283,187 and 5,284,761 which refer to a cell capsule formed by co-extruding a polymer solution and a cell suspension.

Typically, when the cells used for encapsulation and implantation are isolated directly from tissue (primary cells), they are disaggregated, washed, and then encapsulated. See, e.g., Aebischer et al., *Trans. Am. Soc. Artif. Intern. Organs*, 32, pp. 134–7 (1986); Altman et al., *Diabetes*, 35, pp. 625–33 (1986); Chang et al., U.S. Pat. No. 5,084,350); Darquay and Reach, *Diabetologia*, 28, pp. 776–80 (1985); Sugamori and Sefton, *Trans. Am. Soc.Artif. Intern. Organs*, 35, pp. 791–9 (1989).

When immortalized cells or cell lines are to be encapsulated and implanted, they are typically isolated from nutrient-rich cultures. See e.g., Aebischer et al., *Biomaterials*, 12, pp. 50–55 (1981); *Experimental Neurology*, 111, pp. 269–75 (1981) (dopamine-secreting PC12 cells), and Ward et al, WO 93/22427 (IgG-secreting MOPC-31C cells).

Encapsulated cells are usually incubated in vitro and functionally characterized before implantation. Encapsulated cells are often cultured in a defined medium during this pre-implantation stage. Often the medium is a balanced salt solution lacking nutrient additives (e.g. Aebisher, supra; Altman, supra; Chang et al., supra). Alternatively, encapsulated cells are incubated in a nutrient medium such as RPMI 1640, which contains various amino acids, vitamins, inorganic salts and glucose (2 g/L; 11.11 mM) (Animal Cell Culture, Eds. Pollard and Walker, Humana Press Inc., Clifton, N.J., pp. 696–700 (1990)), and is typically supplemented with 5%–15% fetal calf or horse serum.

Cells that are encapsulated and implanted in a host must undergo at least two severe changes in nutrient conditions as compared to in vitro conditions. The first occurs upon encapsulation.

Compared to in vitro conditions, cells in an encapsulated environment are nutrient depleted. This depletion is manifested in two ways. There is a nutrient gradient between the external environment and capsule interior which naturally forms across the membrane. This gradient is further accentuated because molecules do not diffuse freely between the outside host tissue and the cells at every position within the capsule. Cells closer to the capsule surface have preferential access to nutrients diffusing across the capsule jacket. In addition, waste products of cells closer to the capsule surface are more readily eliminated.

A second severe change in the concentration of nutrients, e.g., oxygen and glucose, occurs upon implantation in a host. This is because in vitro oxygen and at least some other nutrient levels are generally much higher than occurs in vivo. Thus the driving force for diffusion of these molecules into the capsule is diminished in vivo.

These changes in the nutrient environment may result in an alteration of one or more cell properties. For example, cell death or reduced long term cell viability can result. In addition, the change in environmental conditions upon implantation may also affect other properties of remaining viable encapsulated cells, such as cell growth rate or the cells' ability to produce a biologically active molecule. Changes in the growth rate of discrete subpopulations of cells may result in a takeover of the capsule by a faster growing subpopulation of cells, potentially leading to an apparent shift in the capsule output characteristics, or other potentially undesirable effects.

One important difference between in vivo implantation conditions and in vitro conditions is the glucose concentration to which the cultured cells are adapted. Another difference between conditions in tissue culture and those at an implantation site is the amount of oxygen available to the cells. Other nutrients may be at significantly different concentrations in culture medium and at a given implantation site.

Cells or tissues that are highly active metabolically are particularly susceptible to the effects of nutrient and oxygen deprivation (hypoxia). Likewise, many endocrine tissues that are normally sustained by dense capillary beds and are thus acclimated to growth in high oxygen and nutrient levels in vivo exhibit this behavior; pancreatic islets of Langerhans and adrenal chromaffin cells are particularly sensitive to hypoxic shock.

Changes in oxygen tension and nutrient stress are known to alter the expression of a large number of genes that affect a variety of cellular functions. Such changes can affect the stability and function of certain mRNAs. For example, the tyrosine hydroxylase mRNA, which encodes the enzyme that catalyzes the rate limiting step in dopamine production, may be affected by nutritional stress.

Further, various heat shock genes, and the expression of metabolic enzymes like those involved in intermediary metabolism (e.g. the glycolytic and gluconeogenic pathways) may be affected by low glucose or amino acid levels.

Importantly, highly-differentiated cell types that are deprived of oxygen can lose their tissue-specific functions until they recover from hypoxic shock, [see, e.g., Wolffe and Tata, *FEBS Letters*, 176, pp. 8–15 (1984)]. Functions that are lost or diminished include the synthesis and modification of proteins. This may affect the production and secretion of the very therapeutic factors that cells are intended to supply to the surrounding host tissue. In addition, hypoxic conditions can in some cases initiate malignant transformation, (see, e.g., H. Goldblatt et at., *Biochemical Medicine*, 7, pp. 241–52 (1973)).

It is desirable to develop a method for implantation involving exposing or acclimating cells to one or more restrictive conditions prior to implantation to reduce alterations in cell properties resulting from the effect of the change in environmental conditions upon implantation, and thus reduce any adverse consequences to the host. It is also desirable to develop cell lines of the cells so prepared. It is also desirable to provide a means for ex vivo study of cells which have undergone changes in the in vivo environment.

SUMMARY OF THE INVENTION

This invention relates to a method for implanting encapsulated cells in a host involving exposing the cells, either in vitro or in vivo, to one or more restrictive conditions for a sufficient period of time to establish a desired cell property in response to the restrictive condition prior to implantation at an implantation site in the host. Preferably, the cell property established by the methods of this invention is substantially maintained following implantation. The encapsulated cells produce a biologically active molecule which may be useful in preventing or treating a disease or disorder, or in providing, restoring or augmenting a metabolic function in the host. Cells produced according to this invention may also be useful for in vitro applications, for diagnostic or other purposes.

DETAILED DESCRIPTION OF THE INVENTION

Figure 1:
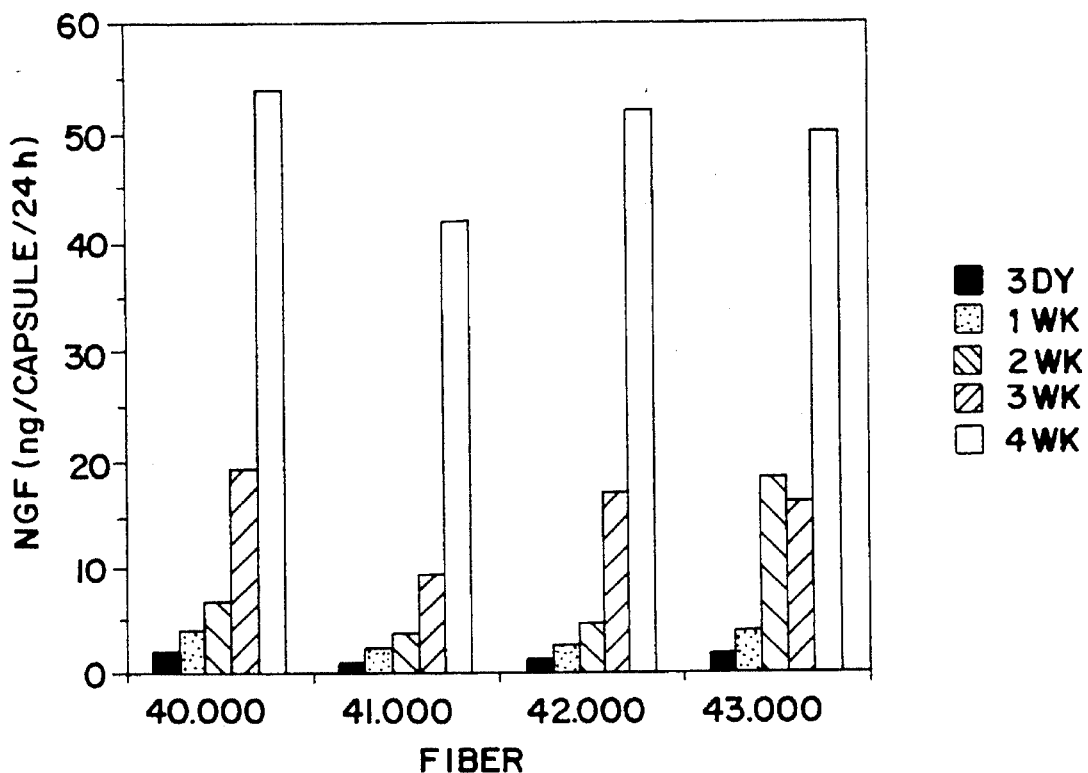
FIG. 1 shows NGF secretion from encapsulated BHK cells incubated in vitro at 50 mmHg in media containing 0.8 g/l glucose (LOW $O_2$/gl). BHK cells were encapsulated in hub-sealed Type 4 double skinned capsules. NGF secretion per capsule per 24 hours, indicated by the height of the bars, was assayed at days 3, 7, 14, 21 and 28.

A "cell property" includes any phenotypic property that can be measured, including cell viability, growth rate, and cellular production of a biologically active molecule. A desired cell property can refer to a change in the level of production of one or more biologically active molecules in response to the restrictive condition.

The term "restrictive condition" means that one or more conditions in which the cells are normally or optimally cultured in vitro has been altered to more closely match the actual or expected condition in vivo at the desired host implantation site.

A "biologically active molecule" is one which may (a) function within the cell in which it is made (e.g. bcl-2 to prevent apoptosis), (b) be expressed on the cell surface and affect the cell's interactions with other cells or biologically active molecules (e.g. a neurotransmitter receptor or cell adhesion molecule), or (c) be released or secreted from the cell in which it is made and exert its effect on a separate target cell (e.g. a neurotransmitter, hormone, growth factor, or cytokine). The biologically active molecules may be useful in treating or preventing a disease or disorder in the host, or may provide, restore or augment one or more metabolic functions in the host.

The term "host" or "recipient" refers to an appropriate animal subject, including mammals and particularly human subjects. The term "recipient" refers to an animal in which cells are exposed to one or more restrictive conditions such that the cells exhibit a desired cell property. The term "host" refers to an animal in which the encapsulated cells that exhibit the desired cell property are implanted.

The term "cells" refers to cells in any form, including but not limited to cells retained in tissue, cell clusters, and individually isolated cells. The cells in the present invention produce a biologically active molecule. The cells may be primary cells or dividing cells that naturally produce the biologically active molecule, or have been genetically engineered to do so.

"A biocompatible capsule" means that the capsule, upon implantation in a host mammal, does not elicit a host response sufficient to detrimentally affect the capsule function or to render it inoperable. Such inoperability may occur, for example, by formation of a fibrotic structure around the capsule limiting diffusion of nutrients to the cells therein. Detrimental effects may also include rejection of the capsule or release of toxic or pyrogenic compounds (e.g. synthetic polymer by-products) from the capsule to surrounding host tissue.

"An immunoisolatory capsule" means that the capsule upon implantation into a mammalian host minimizes the deleterious effects of the host's immune system on the cells within its core, such that the capsule functions for extended periods of time in vivo.

The term "hydrogel" means a three dimensional network of cross-linked hydrophilic polymers. The network is in the form of a gel substantially composed of water, preferably but not limited to gels being greater than 90% water. Cross-linked hydrogels can also be considered solids because they do not flow or deform without appreciable applied shear stress.

In one embodiment, cells are encapsulated in a biocompatible capsule and are exposed to one or more restrictive conditions in vitro before implantation at an implantation site in a host. The cells are exposed to the restrictive condition or conditions for a sufficient period of time to establish a desired cell property in response to the restrictive condition. Preferably the cell property is substantially maintained following implantation of the encapsulated cells at an implantation site in the host.

The restrictive conditions contemplated include alteration in one or more of the following: the temperature, pH, or the barometric pressure, or in the effective concentration of one or more metabolites or cofactors, including but not limited to a sugar, alcohol, carboxylic acid, amino acid, fatty acid, nucleic acid, gas, metal ion or any other biological factor which contributes to the growth, function or viability of the cells, such that the alteration more closely matches the in vivo conditions at the desired implantation site.

It will be appreciated that some nutrients may be present at a lower concentration in vivo than normally encountered in vitro. Alternately, some nutrients may be present at a higher concentration in vivo than normally encountered in vitro.

In addition, the restrictive conditions contemplated by this invention include exposing the encapsulated cells, either in vivo or in vitro, to target cells from a chosen implantation site to produce the desired cell property in the encapsulated cells. See, e.g., Wainer and Heller, "Neuronal Hybrid Cell Lines: Generation, Characterization and Utility" in *Neuronal Cell Lines*, J. Wood [Ed], IRL Press., p. 20 (1992).

Any suitable culture media can be used with the methods of this invention. One of ordinary skill in the art can modify a defined minimal tissue culture medium to achieve a desired concentration of a nutrient of critical gas or other restrictive conditions that characterize a desired implantation site.

When cells are exposed to the restrictive conditions in vitro, the culture conditions may be slowly and continuously altered, or may by altered by one or more step changes to reach the desired restrictive condition.

In a preferred embodiment, cells are exposed to one or more restrictive conditions in vivo by implanting them into a recipient at a chosen implantation site. Once the cells have been exposed to the restrictive conditions for sufficient time to exhibit a desired cell property, the cells are retrieved and can be implanted in a host.

We prefer exposure to the restrictive conditions in vivo because the desired target cell property exhibited by the cells is established by adjustment of all cellular phenotypic traits concurrently to the restrictive conditions. In contrast, acclimation or exposure to the restrictive conditions in vitro may result in establishment of some desired cell properties. However, when these cells are implanted in the host, other cell properties may be altered and affect the desired established target cell property or properties.

Preferably, the recipient and the host are both primates, most preferably the host is human. Preferably the implantation site in the host is the same as in the recipient.

Cells prepared in vivo according to this embodiment may also be maintained under one or more restrictive conditions and used in vitro for diagnostic or other purposes.

In another embodiment, cells are exposed to multiple restrictive conditions in vitro before encapsulation. Preferably, the cells are then encapsulated and exposed to additional restrictive conditions prior to implantation in the host. Exposure to one or more restrictive conditions prior to encapsulation enables one to choose the surviving cells from the initial population and encapsulate only those cells. If the cells used are post-mitotic or otherwise non-dividing cells, the cells may be chosen from the initial population based on their apparent health, and phenotype, preferably as measured by production of the desired biologically active molecule. If the cells used are actively dividing cells, the surviving cells typically will overgrow the initial population.

The time sufficient to establish the desired cell property in response to the restrictive condition will vary according to the cell used, as well as the restrictive conditions. Typically cells will undergo a transition period when initially exposed to the restrictive condition or conditions, during which time the cell phenotype continues to change until the cell property becomes established in response to the restrictive condition. The time required for the transition can be determined by routine experimentation.

In one embodiment, PC12 cells encapsulated in single-skinned semi-permeable membranes are exposed to in vivo restrictive conditions for 6 months in primate brains. After the 6 month implantation period, the cells exhibit a desired cell property in response to the restrictive conditions—i.e., the cells exhibit changed production of neurotransmitters, as measured by the ratio of basal release of L-dopa to dopamine, as well as changes in the relative output of other catecholamines compared to pre-implantation levels.

In another embodiment, adrenal chromaffin cells encapsulated in double skinned semi-permeable membranes are exposed to in vivo restrictive conditions for 55 and 84 days in humans, in the subarachnoid space. After the implantation period, the cells exhibited changed production of neurotransmitters.

A number of different implantation sites are contemplated. These implantation sites include the central nervous system, including the brain and aqueous and vitreous humors of the eye. Preferred sites in the brain include the striatum, the cerebral cortex, subthalamic nuclei and nucleus Basalis of Meynert. Other preferred sites are the cerebrospinal fluid, most preferably the subarachnoid space and the lateral ventricles. This invention also contemplates implantation into the kidney subcapsular site, and intraperitoneal and subcutaneous sites, or any other therapeutically beneficial site.

The local environment varies between implantation sites, between different species. It is likely that the local environment of any given implantation site will vary between individuals of the same species. In general, the metabolite and gas concentrations present in a given implantation site can be approximated from published information or can be determined by one of ordinary skill in the art without undue experimentation.

For example, in humans, it is known that typical partial pressures of oxygen in the body range from about 90 mmHg in arterial blood, to less than 1 mmHg in working muscle tissue. Other typical oxygen pressures are: venous blood (40 mmHg), peritoneal cavity (47 mmHg), and cerebrospinal fluid (59 mmHg).

Likewise, typical glucose values range between 80–120 mg/deciliter (4.4–6.7 mM) in blood-supplied tissue, and 40–70 mg/deciliter (2.2–3.9 mM) in the cerebrospinal fluid (CSF) [See Geigy Scientific Tables, Vol. I, Units of Measurements, Body Fluids, Composition of the Body, Nutrition, 8th Ed., Ed. C. Lentner, CIBA-GEIGY, 1984]. These and other such examples can be found in the Geigy Scientific Tables, incorporated herein by reference. Table I compares the concentrations of a number of compounds present in blood serum and CSF.

TABLE 1

| Compound | Cerebrospinal Fluid | | Blood (Serum) | |
| --- | --- | --- | --- | --- |
| Oxygen | 59 | mmHg | 40 | mmHg |
| Glucose | 100 ± 20 | mg/dL | 55 ± 15 | mg/dL |
| Galactose | 166 ± 99 | µM | 17 ± | µM |
| Glycerol | 13.5 ± 2.5 | µM | 120 ± 65 | µM |
| Lactic acid | 1.6 ± 0.2 | mM | 0.76 ± 0.34 | mM |
| Pyruvic acid | 115 ± 17 | µM | 32 ± 19 | µM |
| Phospholipids | 5.21 ± 0.9 | µM | 2.9 ± 1.2 | µM |
| Fatty acids | 3.5 | µM | 500 | µM |
| cAMP | 21 ± 8 | nM | 11 ± 2.4 | nM |
| cGMP | 2.4 ± 0.5 | nM | 9.5 ± 2.1 | nM |
| Chloride | 125 ± 3 | mM | 102.5 ± 4.5 | mM |
| Phosphorus$_i$ | 0.52 ± 0.07 | mM | 1.05 ± 0.31 | mM |
| Sodium | 145 ± 3.9 | mM | 140 ± 2.38 | mM |
| Calcium | 1.19 ± 0.08 | mM | 2.44 ± 0.1 | mM |
| Magnesium | 0.89 ± 0.17 | mM | 0.78 ± 0.04 | mM |
| Zinc | 0.49 ± 0.12 | µM | 16.7 ± 3.1 | µM |
| Iron | 0.8 ± 0.4 | µM | 17.2 ± 0.75 | µM |
| Copper | 0.25 ± 0.06 | µM | 16.25 ± 0.75 | µM |
| Manganese | 21 ± 6 | nM | 10 ± 2.4 | nM |
| Choline | 8.3 ± 1.7 | µM | 15.5 ± 2.3 | µM |
| Histamine | 87 ± | nM | 3.4 ± 0.7 | nM |
| Norepinephrine | 1.4 ± | nM | 1.65 ± 1.0 | nM |
| Epinephrine | 0.24 ± | nM | 0.13 ± 0.1 | nM |
| Serotonin | 3.9 ± 1.08 | nM | 50 ± 20 | nM |

Molecules including glucose, amino acids, lactate and ribonucleosides are transported across the blood-brain barrier into the CSF to supply CSF-bathed areas such as the ventricles, the sub-arachnoid space and the spinal canal. Galactose concentrations are typically ten-fold higher in the CSF, and pyruvic and lactic acids are more concentrated in the CSF than in blood plasma. In contrast, most amino acids are 5 to 30 times more concentrated in blood than in the CSF (See Geigy Scientific Tables, Vol. I, supra, p. 169).

Other "micronutrient" substances such as vitamin C, folates (vitamin B-complex members), deoxyribonucleosides, and pyridoxine (vitamin B6) are actively transported across the blood-brain barrier into the CSF. In addition, concentrations of ions such as sodium, potassium, calcium, magnesium and chloride are strictly regulated in the CSF (Spector and Johanson, Scientific American, pp. 68–74 (November 1989)).

The metabolites present in culture media are typically chosen to optimize cell growth and viability in tissue culture. The concentration of these compounds deviates from those present at a given implantation site. Often the cells are grown in concentrations of salts and glucose that are higher than those found at desirable implantation sites. For example, RPMI 1640 media contains 11.1 mM glucose, whereas glucose levels are about 4.5 mM in the blood serum and only 2.2–3.9 mM in the CSF.

Similarly, calcium levels in RPMI 1640 are 0.42 mM, whereas calcium levels are 1.2 mM in the CSF and 2.44 mM in the blood serum (Table 1). And zinc ions are present at 0.5 µM in the CSF, 16.7 µM in the blood serum, and absent from RPMI 1640 medium.

In addition, most cells are cultured in vitro at ambient oxygen levels (142 mmHg) or in incubators with ambient humidified air and 5%–7% $CO_2$ (e.g. Aebischer et al., Bio-materials, supra; Ward et al., supra). This may be significantly higher than the oxygen concentration present in vivo at the chosen implantation site in the host.

Further, all tissue culture media lack ephemeral molecules that are present in vivo. These ephemeral molecules are rapidly degraded and are constantly synthesized or replenished in vivo. Some culture media are supplemented with heat-inactivated fetal calf or horse serum to replace some substances, but ephemeral molecules are also generally low or absent in serum. When supplemented with serum, typically less than 20% of the total medium is serum, thus those molecules will be present at best at only one-fifth of the concentration found in serum. In addition, serum-supplemented culture media may contain molecules that do not occur in a discordant host and that may have undesirable effects on the encapsulated cells. Finally, while serum concentrations of most components is reflective of their concentration in the interstitial fluid, concentrations of specific substances may be significantly different between the serum and the interstitial fluid.

The cells used in this invention may be allogeneic to the host (i.e., from the same species as the host) or xenogeneic to the host (i.e., from a different species). We prefer implanting cells in a xenogeneic host. It will be appreciated that preparing cells for implantation in a xenogeneic host will likely involve different restrictive conditions than for an allogeneic host, and may produce a phenotypically different population of cells, with different cell properties.

The cells may be prepared either from a donor (i.e., primary cells or tissues, including adult, neonatal, and fetal cells or tissues) or from cells which replicate in vitro such as immortalized cells or cell lines, including genetically modified cells.

Primary cells can be from non-dividing (post-mitotic) normal tissue, from naturally-dividing (mitotic) cells such as those in the liver, or from pluripotent stem cells like those of the spleen and the bone marrow. Mitotically active cells obtained in vivo can also be from cancerous cells (tumor cells).

Primary cells that may be used according to the present invention include growth factor-responsive neural progenitor stem cells derived from the CNS of mammals [Reynolds and Weiss, Science, 255, pp. 1707–10 (1992); Richards et al., Proc. Natl. Acad. Sci. USA, 89, pp. 8591–95, (1992); Ray et al., Proc. Natl. Acad. Sci. USA, 90, pp. 3602–06, (1993)], primary fibroblasts, Schwann cells, astrocytes, β-TC cells, Hep-G2 cells, ATT20 cells, oligodendrocytes and their precursors, myoblasts, myotubes, adrenal chromaffin cells or tissue of the adrenal medulla. We prefer neural stem cells and adrenal chromaffin cells.

Schwann cells, also preferred, may be prepared according to the method of Bunge (PCT published application WO 92/03536). Encapsulated Schwann cells may be implanted in appropriate areas of the brain to prevent the degeneration of the dopaminergic neurons of the nigral striatal pathway associated with Parkinson's disease. Generally, the preferred implant site will be in or near the striatum. Encapsulating the cells may enhance secretion of trophic factors since the cells will not be in proximal contact with neurons, and myelination will not occur. Other glial cell types may be encapsulated and implanted for this purpose, including astrocytes and oligodendrocytes.

Techniques for isolating cells or tissues that produce a selected product are known, or can be adapted from known procedures. For example, islets of Langerhans can be isolated from a large-animal pancreas (e.g., human or porcine) using a combination of mechanical distention and collagenase digestion, as described by Scharp, et al., U.S. Pat. No. 4,868,121. Islets may be isolated from small animals such as rats by the method of Scharp, et al., *Diabetes* 29, suppl. 1, pp. 19–30 (1980).

Similarly, hepatocytes can be isolated from liver tissue using collagenase digestion followed by tissue fractionation, as described by Sun, et al., *Biomat. Art. Cells, Art. Org.*, 15, pp. 483–496 (1987). Adrenal chromaffin cells may be isolated by known methods [Livett, *Physiology Reviews*, 64, pp. 1103–61 (1984); Sagen et al., U.S. Pat. No. 4,753,635].

Immortalized cells can be from primary sources, or can have been selected from cells transformed with viruses, viral gene products, oncogenes, or other immortalizing genes or gene products. Examples of publicly-available cell lines suitable for the practice of this invention include: baby hamster kidney (BHK), chinese hamster ovary (CHO), mouse fibroblast (L–M), NIH Swiss mouse embryo (NIH/3T3), African green monkey cell lines (including COS-a, COS-7, BSC-1, BSC-40, BMT-10 and Vero), rat adrenal pheochromocytoma (PC12), PC12A, rat glial tumor (C6) cells, RAJI (human lymphoma) cells, MOPC-31C mouse plasmacytoma cells, MN9D, MN9H cells and ripTAg transgenic mouse derived cells. We prefer BHK and PC12 cells.

Techniques for cell immortalization are described in Land et al., *Nature* 304, pp. 596–602 (1983) and in Cepko, *Neuron* 1, pp. 345–353 (1988). Candidate cell lines include genetically engineered beta-cell lines which secrete insulin such as NIT cells (Hamaguchi, et al., *Diabetes* 40, p. 842 (1991)) and RIN cells (Chick, et al., *Proc. Natl. Acad. Sci. USA*, 74, pp. 628–632 (1977)), ATT cells (Hughes, et al., *Proc. Natl. Acad. Sci. USA*, 89, pp. 688–692 (1992)), CHO cells (Matsumoto, et al., *Proc. Natl. Acad. Sci. USA*, 87, pp. 9133–37, (1990)), and β-TC-3 cells (Tal, et al., *Mol. Cell Biol.*, 12, pp. 422–32, (1992)).

The cells of this invention either naturally produce a biologically active molecule, or can be genetically engineered to do so. For example, fibroblasts can be transfected with an expression vector for the chosen product (e.g., nerve growth factor, erythropoietin, insulin, CNTF or Factor VIII).

Examples of biologically active molecules that may be used to treat diseases or disorders include insulin, which may be used to treat diabetes, parathyroid hormone, which may be used to treat hypoparathyroidism, erythropoietin, which may be used to treat anemia, and gamma-aminobutyric acid to treat epilepsy.

Similarly, biologically active molecules such as trophic and growth factors may be used to treat or prevent neurodegenerative conditions such as Huntington's chorea and Alzheimer's disease, AIDS-related dementia, and Parkinson's disease. Biological response factors such as lymphokines or cytokines can enhance a patient's immune system or act as an anti-inflammatory agent, and can be useful for treating certain chronic infectious diseases or cancers. Additionally, catecholamines, endorphins, enkephalins, and other opioid peptides may also be supplied by encapsulated cells to treat pain.

Encapsulated cells may be used to supply a biologically active molecule useful in correcting an enzymatic deficiency. One example of such a deficiency is fulminant hepatic failure, wherein liver tissue can no longer remove toxins or excrete metabolic waste products. Another example is phenylketonuria, wherein the amino acid phenylalanine builds up to dangerous levels in an affected infant's bloodstream.

Alternatively, the encapsulated cells may produce biologically active molecules that remove deleterious or undesirable products from the host. For example, the encapsulated cells may produce biologically active molecules which "scavenge" cholesterol from the host.

The biologically active molecules of this invention include hormones, cytokines, growth factors, trophic factors, angiogenesis factors, antibodies, blood coagulation factors, lymphokines, enzymes, and other therapeutic agents or agonists, precursors, active analogs, or active fragments thereof. These include catecholamines, endorphins, enkephalins, and other opioid peptides, dynorphin, insulin, factor VIII, erythropoietin, substance P, nerve growth factor (NGF), glial-cell-line-derived neurotrophic factor (GDNF), platelet-derived growth factor (PDGF), epidermal growth factor (EGF), brain-derived neurotrophic factor (BDNF), neurotrophin-3 (NT-3), neurotrophin-4/5 (NT-4/5) an array of fibroblast growth factors, ciliary neurotrophic factor (CNTF), CNTF-related molecules and insulin-like growth factors I, II and III.

In one embodiment, the biologically active molecule is a neurotransmitter. Such neurotransmitters include dopamine, gamma-aminobutyric acid (GABA), serotonin, acetylcholine, norepinephrine, epinephrine, glutamic acid, and other peptide neurotransmitters, preferably dopamine, norepinephrine or epinephrine. In addition, the biologically active molecule may be an agonist, analog, derivative or fragment of a neurotransmitter, including, for example, L-dopa, a dopamine precursor.

In another embodiment, the acclimated cells secrete antinociceptive agents including catecholamines, enkephalins, opioid peptides or agonists or analogs thereof, can be used or mixtures thereof. Preferably catecholamines or enkephalins are secreted, most preferably a mixture of catecholamines and enkephalins.

The capsules useful in this invention typically have at least one semipermeable outer surface membrane or jacket surrounding a cell-containing core. The jacket permits the diffusion of nutrients, biologically active molecules and other selected products through the capsule. The capsule is biocompatible, and preferably immunoisolatory. The core contains isolated cells, either suspended in a liquid medium or immobilized within a hydrogel matrix.

The choice of materials used to construct the capsule is determined by a number of factors and is described in detail in Dionne WO 92/19195. Briefly, various polymers and polymer blends can be used to manufacture the capsule jacket. Polymeric membranes forming the capsule may include polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, PAN/PVC, as well as derivatives, copolymers and mixtures thereof.

Capsules may be formed by any suitable method known in the art. One such method involves coextrusion of a polymeric casting solution and a coagulant which can include biological tissue fragments, organelles, or suspensions of cells and/or other therapeutic agents. The jacket may have a single skin (Type 1, 2), or a double skin (Type 4). A single-skinned hollow fiber may be produced by quenching only one of the surfaces of the polymer solution as it is co-extruded. A double-skinned hollow fiber may be produced by quenching both surfaces of the polymer solution as it is co-extruded. Typically, a greater percentage of the surface of Type 1 hollow fibers is occupied by macropores compared to Type 4 hollow fibers. Type 2 hollow fibers are intermediate. See, e.g., Dionne, WO 92/19195 and U.S. Pat. Nos. 5,158,881, 5,283,187 and 5,284,761, incorporated herein by reference.

Numerous capsule configurations, such as cylindrical, disk-shaped or spherical are possible.

The jacket of the vehicle will have a pore size that determines the molecular weight cut off (MWCO) of the permselective membrane. Molecules larger than the MWCO are physically prohibited from traversing the membrane. The membrane pore size is chosen to permit the particular factors being produced by the cells to diffuse out of the vehicle, but to exclude the entry of host immune response factors into the vehicle. Typically the MWCO ranges between 50 and 200 kD, preferably between 50 and 100 kD. The most suitable membrane composition will also minimize reactivity between host immune effector molecules known to be present at the selected implantation site, and the vehicle's outer membrane components.

The core of the immunoisolatory vehicle is constructed to provide a suitable local environment for the particular cells isolated therein. The core can comprise a liquid medium sufficient to maintain cell growth. Liquid cores are particularly suitable for maintaining transformed cell lines like PC12 cells. Alternatively, the core can comprise a gel matrix. The gel matrix may be composed of hydrogel (alginate, "Vitrogen", etc.) or extracellular matrix components. See, e.g., Dionne WO 92/19195.

Compositions that form hydrogels fall into three general classes. The first class carries a net negative charge (e.g., alginate). The second class carries a net positive charge (e.g., collagen and laminin). Examples of commercially available extracellular matrix components include Matrigel™ and Vitrogen™. The third class is net neutral in charge (e.g., highly crosslinked polyethylene oxide, or polyvinylalcohol).

Cores made of a hydrogel matrix are particularly suitable for maintaining cells or tissues that tend to form agglomerates or aggregates, such as the cells in islets of Langerhans, or adrenal chromaffin cells.

Factors influencing the number of cells or amount of tissue to be loaded within the core of the capsule include (1) capsule size and geometry; (2) mitotic activity of cells within the capsule, and (3) viscosity requirements for core preparation and or loading. These factors are described in detail in Dionne WO 92/19195.

Implanted macrocapsules can be readily retrieved using a tether fabricated onto the capsule. Microcapsules can be retrieved using aspiration or any other suitable method. In particular, retrieval of microcapsules is facilitated by use of a pouch device, as described in PCT/US93/07076.

Any suitable method of sealing the capsule may be used, including the employment of polymer adhesives and/or crimping, knotting and heat sealing. These sealing techniques are known in the art. In addition, any suitable "dry" sealing method can also be used. In such methods, a substantially non-porous fitting is provided through which the cell-containing solution is introduced. Subsequent to filling, the capsule is sealed. Such a method is described in copending U.S. application Ser. No. 08/082,407, herein incorporated by reference.

One or more in vitro assays are preferably used to establish functionality of capsules prior to implantation in vivo. Assays or diagnostic tests well known in the art can be used for these purposes. See, e.g., *Methods In Enzymology*, Abelson [Ed], Academic Press, 1993. For example, an ELISA (enzyme-linked immunosorbent assay), chromatographic or enzymatic assay, or bioassay specific for the secreted product can be used. If desired, secretory function of an implant can be monitored over time by collecting appropriate samples (e.g., serum) from the recipient and assaying them. If the recipient is a primate, microdialysis may be used.

The number of capsules and capsule size should be sufficient to produce a therapeutic effect upon implantation is determined by the amount of biological activity required for the particular application. In the case of secretory cells releasing therapeutic substances, standard dosage considerations and criteria known to the art are used to determine the amount of secretory substance required. Factors to be considered are discussed in Dionne, WO 92/19195.

Implantation of the encapsulated cells is performed under sterile conditions. Generally, the capsule is implanted at a site in the host which will allow appropriate delivery of the secreted product or function to the host and of nutrients to the implanted cells or tissue, and will also allow access to the capsule for retrieval and/or replacement.

The invention will now be further illustrated by the following examples, which are not to be viewed as limiting in any way.

EXAMPLES

EXAMPLE 1: NGF secretion by encapsulated BHK cells exposed to a low oxygen and glucose environment.

BHK-NGF Cell Line Production

A BHK cell line secreting NGF was produced and exposed to a low oxygen and glucose environment.

A 2.51 kb fragment containing approximately 37 bp of the 3+ end of the first intron, the double ATG sequence believed to be the protein translation start for pre-pro-NGF and the complete coding sequence and entire 3' untranslated region of the human gene (Hoyle et al., *Neuron*, 10, pp. 1019–34, 1993) was subcloned into the DHFR-based pNUT expression vector immediately downstream from the mouse metallothionein-1 promotor (−650 to +7) and the first intron of the rat insulin II gene (Baetge et al., *Proc. Natl. Acad. Sci.*, 83, pp. 5454–58 (1986).

Baby hamster kidney (BHK) cells were transfected with the pNUT-βNGF construct using the calcium phosphate method. BHK cells were grown in DMEM containing 10% fetal bovine serum, 1×pen/strep/amph B (0.8 g/l), and L-glutamine (GIBCO) in 5% $CO_2$ and at 37° C. Transfected BHK cells were selected in medium containing 200 μM methotrexate (Sigma) for 3–4 weeks and resistant cells were maintained as a polyclonal population either with or without 200 μM methotrexate.

Preparation of PAN/PVC fibers

Permselective hollow fibers were prepared via a dry jet-wet spinning technique [Cabasso, *Hollow Fiber Membranes*, vol. 12, *Kirk-Othmer Encyclopedia of Chemical Technology*, Wiley, N.Y., 3rd Ed., pp. 492–517, 1980; Dionne, WO 92/19195]. Asymmetric hollow fibers were cast from solutions of 10% polyacrylonitrile polyvinyl chloride (PAN/PVC) copolymer in dimethyl sulfoxide (w/w) and quenched directly into a coagulant bath. The resulting double skinned (Type 4) fibers were collected into a non-solvent water bath, glycerinated, and dried.

Preparation of Matrix

Eight ml of rat tail collagen (Type IV, Collaborative, lot 91-1083) were added to 1 ml of phenol red/phosphate buffered saline (PBS) and the solution adjusted to pH 7.0. Eight ml of Vitrogen® (Celtrix, Palo Alto, Calif.; Lot 92H176) were added to 2 ml of phenol red/PBS. Equal volumes of the collagen and Vitrogen® solutions were mixed together to form the matrix solution.

Loading And Sealing Procedure

Single cell suspensions of NGF-producing BHK cells grown to 90% confluency were rinsed with PBS (lacking calcium and magnesium), trypsinized for approximately 1 minute and pelleted by centrifugation at 1000 rpm for 3 minutes. The cells were resuspended in medium to a final cell concentration of $2\times10^7$ cells/ml. This cell suspension was then mixed 1:1 with collagen/Vitrogen® matrix solution, bringing the final cell concentration to $1\times10^7$ cells/ml.

Cells were gently mixed in matrix to assure even distribution of the slurry prior to encapsulation. 2.5 microliters (ul) of the cell/matrix slurry (10,000 cells/ul) were loaded into a fiber using a 24-gauge beveled catheter tip and a Hamilton syringe.

Capsules were sealed by mounting a 1–1.1 cm length of dry hollow fiber onto a hub with a septal fixture at the proximal end which has loading access for cells to be injected into the lumen of the device. After infusing 2.5 μl of the cellular suspension, the septum was cracked off and the access port sealed using a light-cured acrylate (Luxtrak™ LCM 24, ICI Resins US, Wilmington, Mass.) ("hub" sealed). The capsules were subsequently "tethered" by placing a 1.5 cm 0.020" silastic tube over the acrylic hub.

Capsules were acclimated for three days at ambient oxygen levels, and tested for baseline NGF secretion. Three-day old medium was replaced with 1 milliliter (ml) of fresh medium.

Capsules were then placed in a 24-well plate containing low glucose (0.8 mg/l) and low oxygen (50 mmHg) or high glucose (5.5 mg/l) and ambient (142 mmHg) oxygen levels. Media were changed and NGF assays performed every 7 days. One day prior to a change, fresh media were brought to the appropriate oxygen concentrations for each acclimation condition. Encapsulated cells were cultured in this way for four weeks.

NGF levels were determined by ELISA (enzyme-linked immunosorbent assay) on days 0, 3, 7, 14, 21, and 28. Representative capsules were fixed with 4% paraformaldehyde for histological determination of cell viability profiles.

Following fixation in 4% paraformaldehyde, the retrieved capsules were rinsed with phosphate buffered saline (PBS), dehydrated in graded alcohol up to 95% and embedded in glycol methacrylate infiltration solution (Historesine Mounting Medium, Reichert-Jung). Three micron thick sections were cut on a microtome (Supercut 2065, Leica), mounted on glass slides and stained with cresyl violet.

NGF ELISA

The quantification of hNGF released from encapsulated BHK/NGF cells was performed as follows. Nunc-Immuno Maxisorp ELISA plates were coated with 150 μl per well of anti-mouse-β (2.5S) NGF at 1 ng/ml in coating buffer (1×PBS without $CaCl_2$ and without $MgCl_2$/0.1% sodium azide; pH 9.6) and incubated at 37° C. for at least 2 hours or alternatively at 4° C. overnight.

The coating solution was discarded, the wells were washed 3× with 300 μl wash buffer (50 mm Tris-HCl/200 mm NaCl/1% Triton X-100/0.1% sodium azide; pH 7.0) and blocked with 300 μl of coating solution containing 10 mg/ml of BSA at room temperature for 30 min. The wells were then washed 3×with 300 μl wash buffer. Conditioned medium samples were diluted 1:1 in 2× sample buffer (the sample buffer is the same as wash buffer, only with 2% BSA), with 10 μl of the prepared samples loaded into the wells. The plates were incubated for at least 2 hours at 37° C. or overnight at 4° C.

Each well was emptied, washed 3× with 300 μl of Wash buffer and 100 μl of 4U/ml of anti-mouse-β (2.5S) NGF-β-gal conjugate was added. The plates were incubated at 37° C. for at least 1 hour. Each well was emptied, washed 3× with 300 of wash buffer, and 200 μl of chlorophenol red-β-D-galactopyranoside substrate solution (40 mg CPRG in 100 mm Hepes/150 mm NaCl/2 mm $MgCl_2$/0.1% sodium azide/1% BSA; pH 7.0) added. The plates were incubated at 37° C. for 30 min to one hr or until color development was sufficient for photometric determination at 570 nm.

Results

Figure 2:
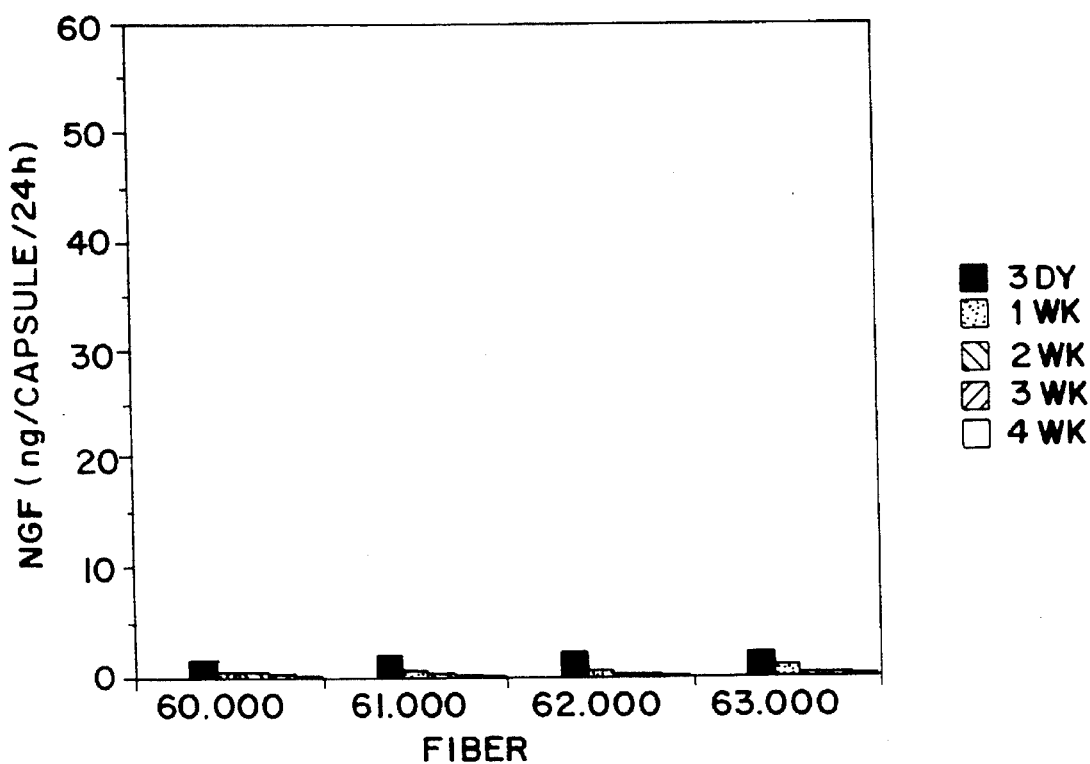
FIG. 2 shows encapsulated BHK cells incubated in vitro at 142 mmHg in media containing 5.5 g/l glucose (HIGH $O_2$/gl). BHK cells were encapsulated in hub-sealed, Type 4 (T4) capsules and NGF secretion per capsule per 24 hours, indicated by the height of the bars, was measured at days 3, 7, 14, 21 and 28.

The NGF release per capsule as a function of time under the two environmental conditions is shown for the 10% Type 4 fiber with hub seals in FIGS. 1 and 2. Data is expressed as ng NGF released per capsule per 24 hours. Production of NGF per capsule increased over the evaluation period.

EXAMPLE 2: NGF secretion by BHK cells acclimated after encapsulation in capsules having varying hydraulic permeabilities BHK-NGF cells as described in Example 1 were used for this example. Hollow fibers were prepared as described in Example 1, except that macrocapsules were prepared using 12.5% and 15% PAN/PVC, as well as 10% PAN/PVC in the casting solution. PAN/PVC double skinned fibers (T4) were 1 cm long and had the following characteristics:

| % Solids | I.D. (μm) | Hydraulic Permeability |
|---|---|---|
| 10 | 721 | 60 |
| 12.5 | 733 | 20 |
| 15 | 746 | 13 |

(hydraulic permeability in ml/min/m$^2$/mmHg)

BHK-NGF cells were loaded into the three types of macrocapsule, and sealed as described in Example 1. The capsules were exposed to low glucose and low oxygen conditions for four weeks and tested for NGF release as described in Example 1.

Figure 3A:
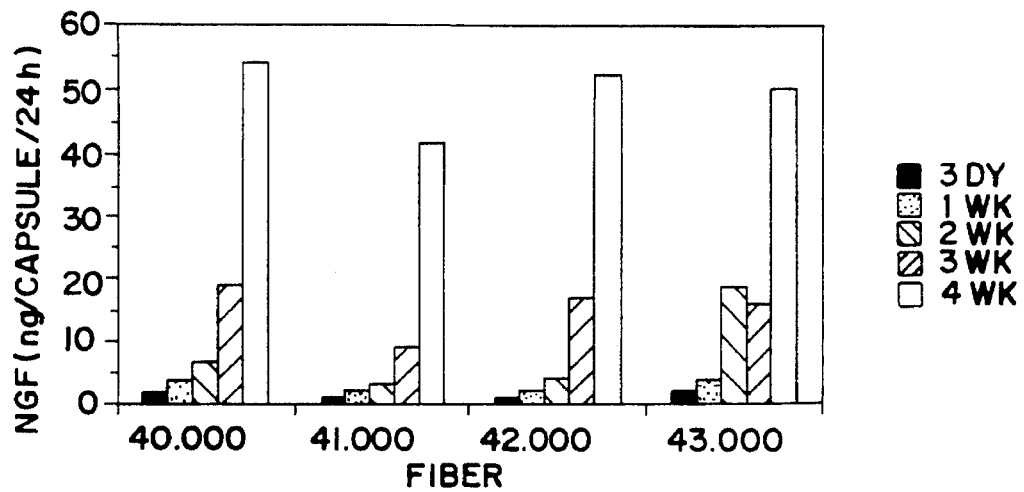
FIG. 3 shows NGF secretion from encapsulated BHK cells incubated in vitro in LOW $O_2$/gl media, as in FIG. 1, over time in hub-sealed, Type 4 (T4) capsules made from either (a) 10% PAN/PVC, (b) 12.5% PAN/PVC, or (c) 15% PAN/PVC. NGF secretion per capsule per 24 hours, indicated by the height of the bars, was measured at days 3, 7, 14, 21 and 28.
Figure 3B:
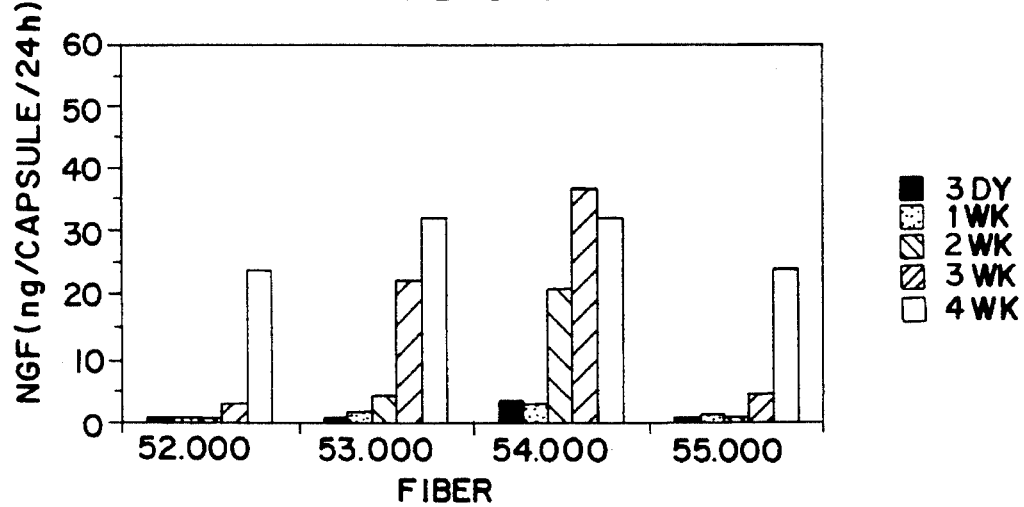
Figure 3C:
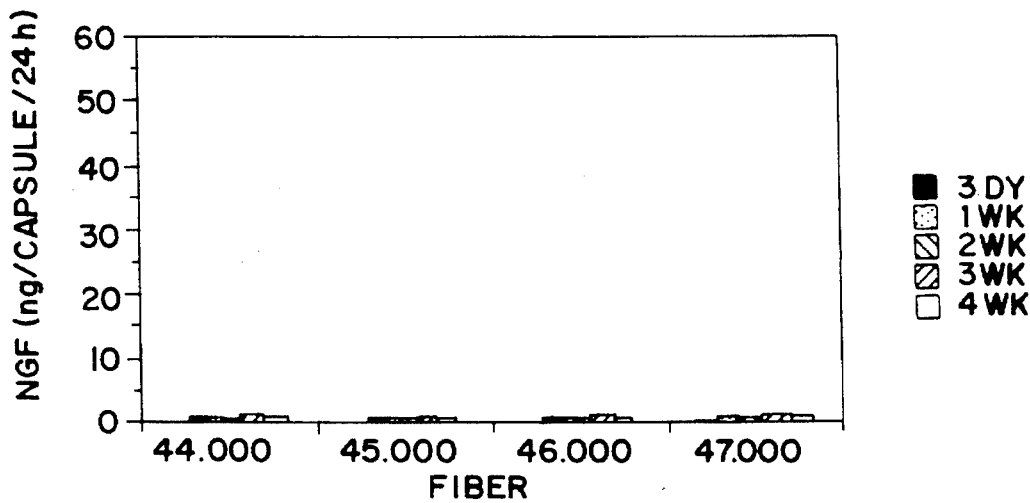
Figure 4A:
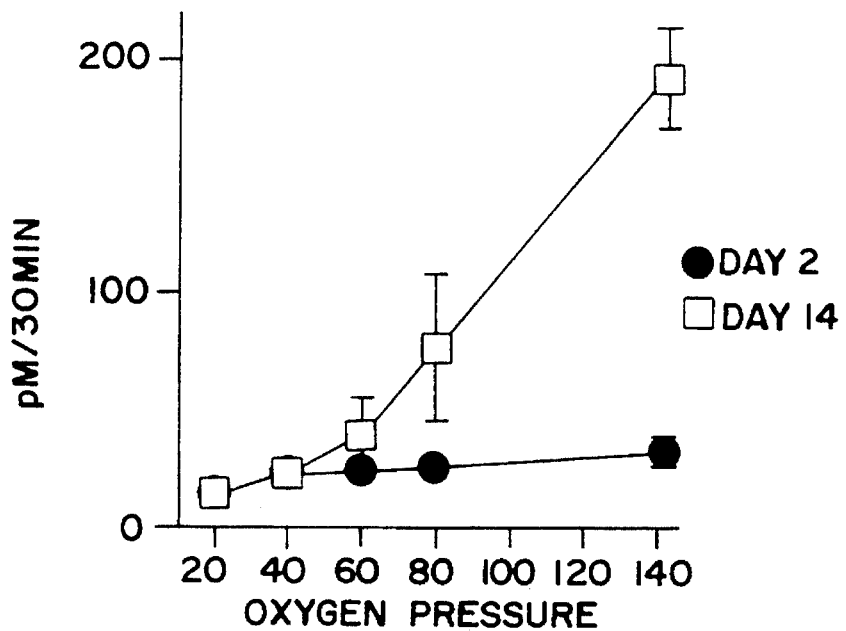
FIG. 4 shows release of norepinephrine (NE) and epinephrine (EPI) as a function of oxygen pressure by encapsulated adrenal chromaffin cells cultured in vitro for 14 days at 20, 40, 60, 80 and 140 mmHg $O_2$. Release was measured at day 2 and day 14. Panel A shows basal NE release; panel B shows $K^+$-evoked NE release; panel C shows basal EPI release, panel D shows $K^+$-evoked EPI release.
Figure 4B:
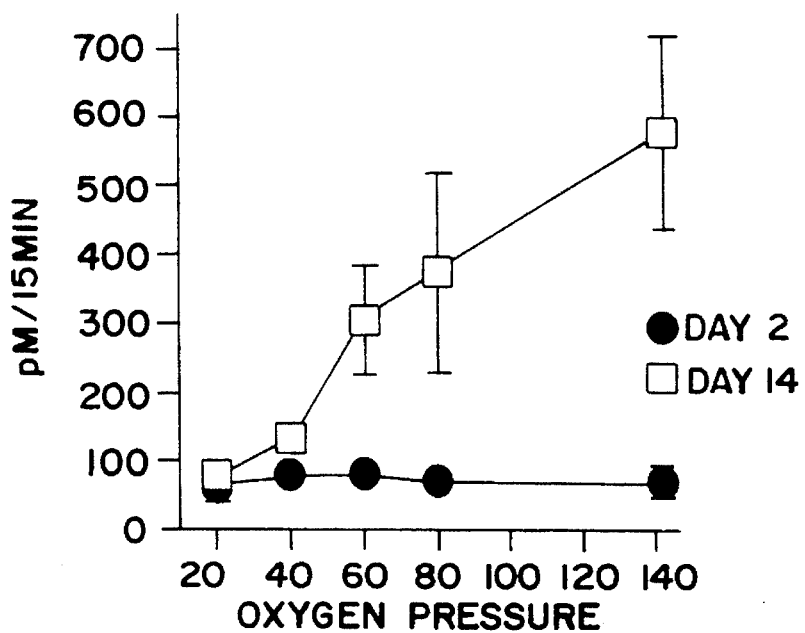
Figure 4C:
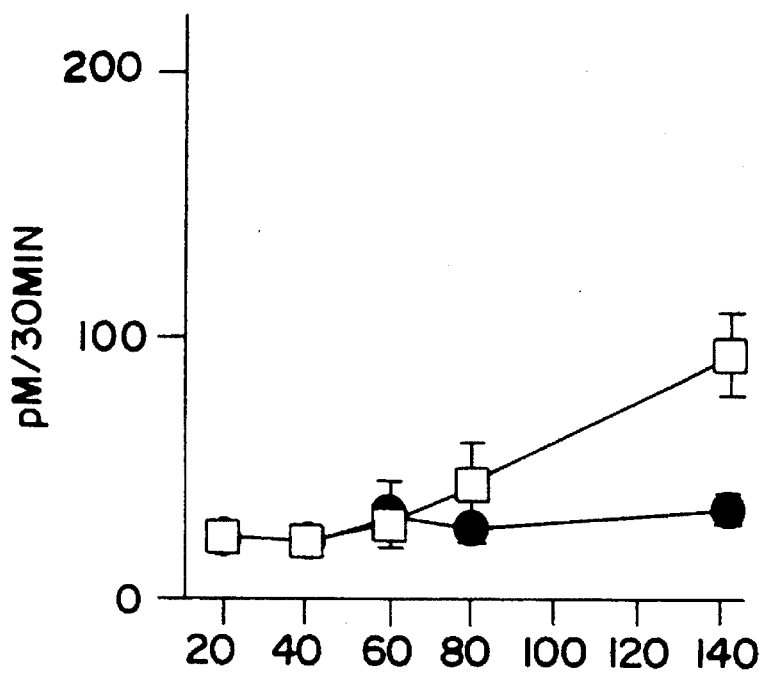
Figure 4D:
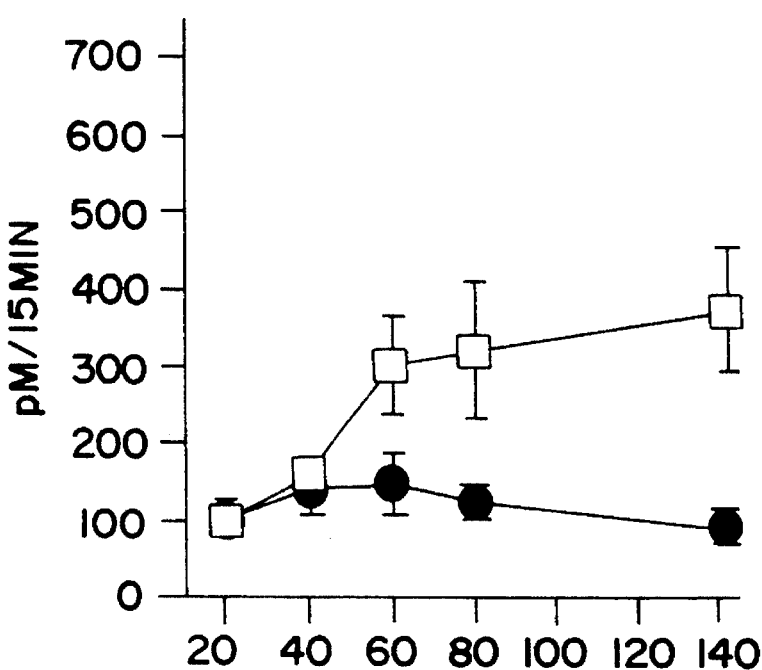

The NGF output from the three different capsule types as a function of time is shown in FIG. 3. The average NGF release from the 10% PAN/PVC capsule was about 50 ng/capsule/24 hr after 4 weeks, compared to about 30 ng/capsule/24 hours for the 12.5% PAN/PVC capsule. The 15% PAN/PVC capsule produced no detectable levels of NGF after 1, 2, 3 or 4 weeks. Histological examination of the capsules confirmed that healthy cell clusters were present in 10% and 12.5% PAN/PVC capsules. Only dead cells were present in 15% PAN/PVC capsules after 4 weeks.

EXAMPLE 3: Encapsulated BHK-NGF cells are implanted into a host.

The encapsulated cells of Example 1 are exposed to the low oxygen and glucose concentrations of Example 1 until the level of NGF secretion from the BHK cells is stable under these restrictive conditions. The encapsulated cells are implanted into a human host. Implantation sites include the lateral ventricles and striatum of the brain. Procedures for implantation of capsules into the brain are published in Aebischer et al., WO 93/00127, incorporated herein by reference.

EXAMPLE 4: Encapsulated adrenal chromaffin cells exposed to in vitro restrictive conditions.

Bovine adrenal chromaffin cells were recovered from adrenal glands by collagenase digestion as described in Livett, *Physiol. Rev.*, 64, pp. 1103–62 (1984). Adrenal cell aggregates were immobilized in a 1.5% alginate matrix crosslinked with $CaCl_2$ and encapsulated in double skinned Type 4, immunoisolatory PAN/PVC hollow fiber membranes (ID 750 μm, wall 85 μm, mMWCO 60 kD), substantially as described in WO92/19195.

The encapsulated cells were cultured for 2 weeks at $pO_2$ of 20, 40, 60, 80, and 142 mmHg. The cells were tested for basal and $K^+$-evoked catecholamine release on day 2 and 14. After 14 days, the capsules were fixed in 4% paraformaldehyde and processed for histology, sectioned, and assessed morphologically.

Catecholamines were analyzed by HPLC using electrochemical detection. The chromatographic system used a coulometric multielectrode detector (model 5100A, ESA, Inc.), a Hitachi L6200 pump (Hitachi, Inc.), and a Hypersil 150 mm×4.6 mm, 3 micron ODS column (Keystone Scientific Inc.) fitted with an MPLC NewGuard Column (Applied Biosystems, Inc.). Runs were performed at 26° C.

The mobile phase consisted of 75 mM $NaH_2PO_4$, 1.4 mM octanesulfonic acid, 0.274 mM EDTA and 100 mL/L $CH_3CN$. The pH was adjusted to 3.0 using concentrated phosphoric acid. The flow rate was maintained at 1.0 mL/min.

The detector was equipped with a preinjector guard cell (model 5020) operating at +450 mV and a high resolution dual analytical cell (nodel 5011) operating in an oxidative screen mode at −40 mV and +400 mV for electrode 1 and 2, respectively. Analytes were measured at detector 2.

Triplicate standards were used to validate detection thresholds of 52 fmol for L-Dopa (L-3,4-Dihydroxyphenylalamine), Dopac (3,4-Dihydroxyphenylacetic acid), norepinephrine (NE) and dopamine (DA), and of 104 fmol on-column for HVA (Homovanillic acid) with percent standard deviation ranges at threshold of 2–5%, 9–12%, 15–24% and 6–17%, respectively. Singlicate 7-point standard curves were linear across an on-column analyte range of 52 to 3300 fmol for L-Dopa, Dopac, NE and DA, and 104 to 6600 fmoles for HVA, with $r^2$ values of 0.999, 0.998, 0.999, and 0.999, respectively.

Data were captured and peak areas integrated using a Waters 845 VAX Chromatography Workstation.

The results are shown in FIG. 4. Data is expressed as picomoles per 30 minutes (basal output) or picomoles per 15 minutes ($K^+$-evoked output). At higher $O_2$ concentrations, the basal, and more particularly the $K^+$-evoked, release of both norepinephrine (NE) and epinephrine (EPI) was higher at day 14 than at day 2. Thus, exposure of encapsulated cells to restrictive conditions resulted in alteration of one or more cell properties.

EXAMPLE 5: Encapsulated adrenal chromaffin cells exposed to in vivo restrictive conditions.

Bovine adrenal chromaffin cells were prepared as described in Example 4. Adrenal cell aggregates were immobilized in a 1.5% alginate matrix crosslinked with $CaCl_2$ and encapsulated in either single skinned Type 2, immunoisolatory PAN/PVC hollow fiber membranes (ID 500 μm, wall 70–90 μm, mMWCO 60 kD), or double skinned Type 4 immunoisolatory PAN/PVC hollow fiber membranes (ID 500 μm, wall 70–90 μm, mMWCO 60 kD), substantially as described in WO92/19195.

The encapsulated cells were exposed to in vivo restrictive conditions by implantation into the striatum in rat recipients. Two capsules were implanted per rat, bilaterally. Following midline incision, a hole was drilled in the skull at coordinates +0.5 mm to bregma, 3.0 mm lateral with the incisor bar set −0.3 mm below the intra-aural line. The capsules were lowered 7 mm deep to the dura.

Capsules were assayed for catecholamine production before implantation and after a 6 week period in vivo. Catecholamines were assayed as described in Example 4.

Figure 5A:
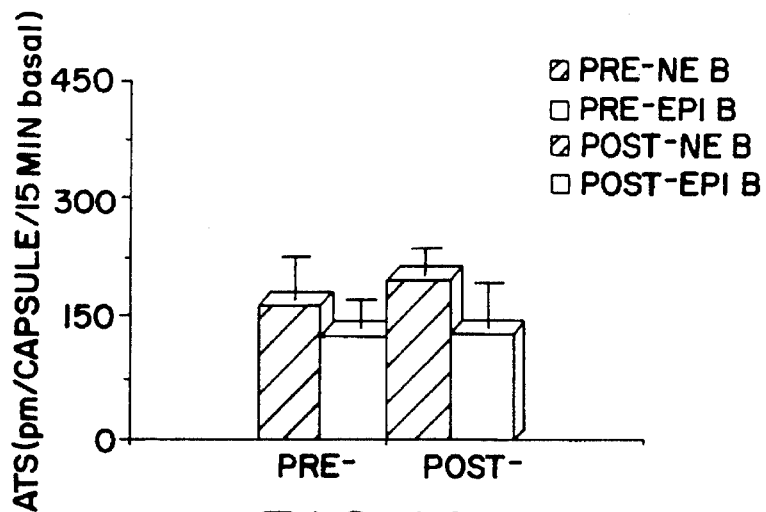
FIG. 5 shows release of catecholamines by calf adrenal chromaffin cells encapsulated in Type 2 capsules, prior to implantation and following retrieval after a 6 week implantation period. Panel A shows the basal release of NE and EPI before and after the implantation period. Panel B shows that nicotine-stimulated release of NE and EPI before and after the implantation period. Panel C shows the $K^+$-evoked release of NE and EPI before and after the implantation period.
Figure 5B:
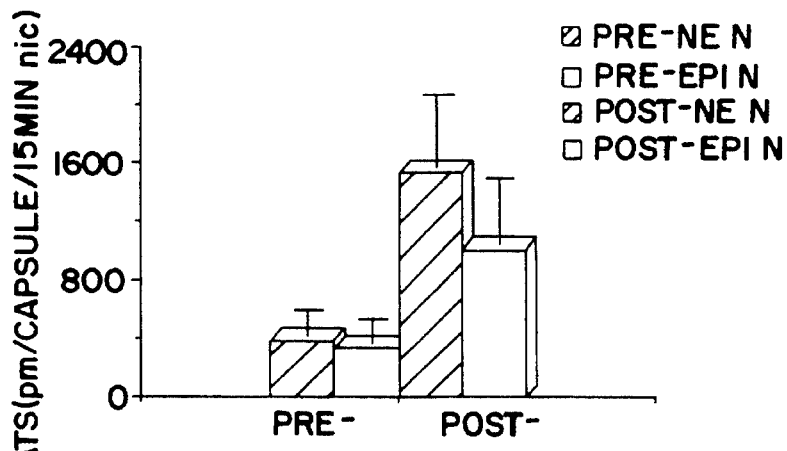
Figure 5C:
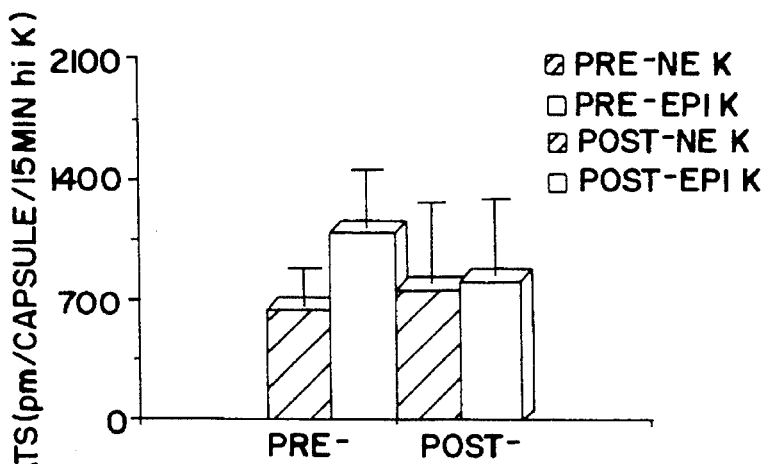

FIG. 5 shows the results obtained using Type 2 membranes. Data is expressed as picomoles per capsule per 15 minutes. The levels of basal (Panel A) and $K^+$-evoked (Panel C) NE and EPI release were similar before and after the 6 week implantation period. However, the level of nicotine evoked (Panel B) NE and EPI release after the 6 week in vivo exposure period was higher than the pre-implantation level.

Figure 6A:
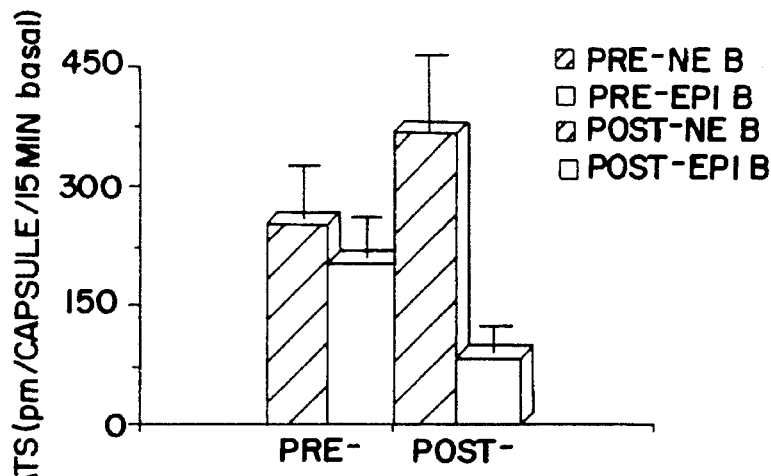
FIG. 6 shows release of catecholamines by calf adrenal chromaffin cells encapsulated in Type 4 capsules, prior to implantation and following retrieval after a 6 week implantation period. Panel A shows the basal release of NE and EPI before and after the implantation period. Panel B shows that nicotine-stimulated release of NE and EPI before and after the implantation period. Panel C shows the $K^+$-evoked release of NE and EPI before and after the implantation period.
Figure 6B:
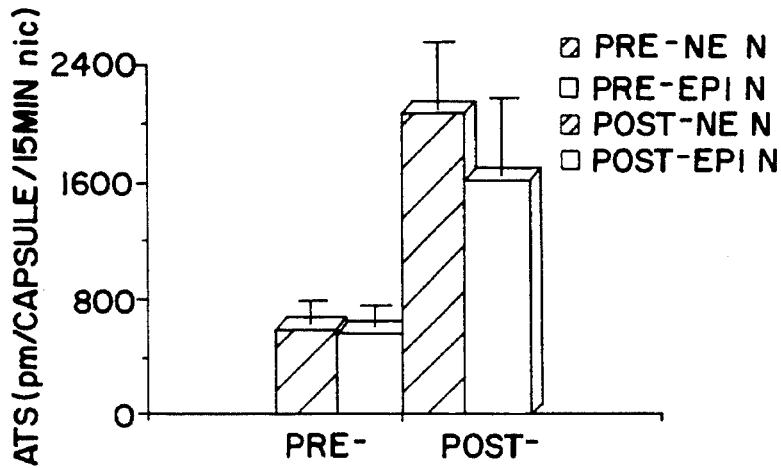
Figure 6C:
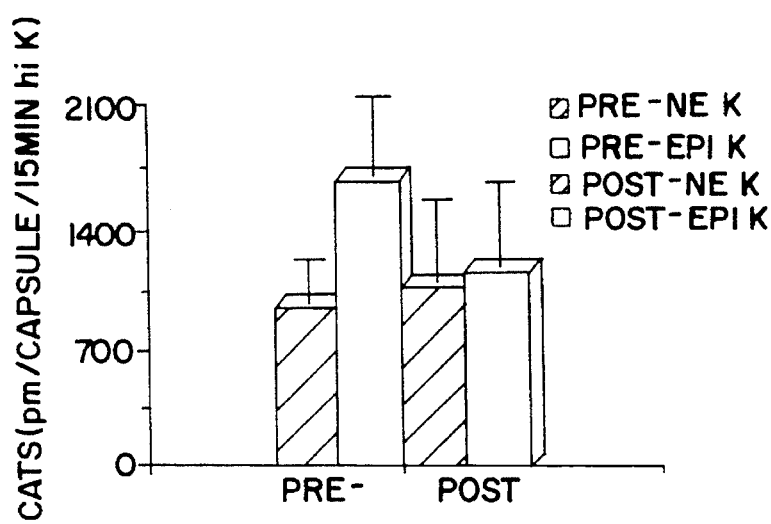

FIG. 6 shows the results obtained using Type 4 membranes. The levels of $K^+$-evoked (Panel C) NE and EPI release were similar before and after the 6 week implantation period. However, the level of nicotine evoked (Panel B) NE and EPI release after the 6 week in vivo exposure period was higher than the pre-implantation level. In addition, there were differences between the basal level of catecholamine release before and after the 6 week implantation period (Panel A).

EXAMPLE 6: Encapsulated adrenal chromaffin cells exposed to in vivo restrictive conditions.

Bovine adrenal chromaffin cells were prepared as described in Example 4. Adrenal cell aggregates were immobilized in a 1.5% alginate matrix crosslinked with $CaCl_2$ and encapsulated in double skinned Type 4, immunoisolatory PAN/PVC hollow fiber membranes (ID 500 μm, wall 70–90 μm, mMWCO 60 kD), substantially as described in WO92/19195.

The encapsulated cells were exposed to in vivo restrictive conditions by implantation into the spinal subarachnoid space in rat recipients. Surgical procedures were performed substantially as described in Aebischer et al., WO 93/00127.

Capsules were assayed for catecholamine production before implantation and after a 6 week period in vivo. Catecholamines were assayed as described in Example 4. Data is expressed as picomoles per capsule per 30 minutes.

Figure 7A:
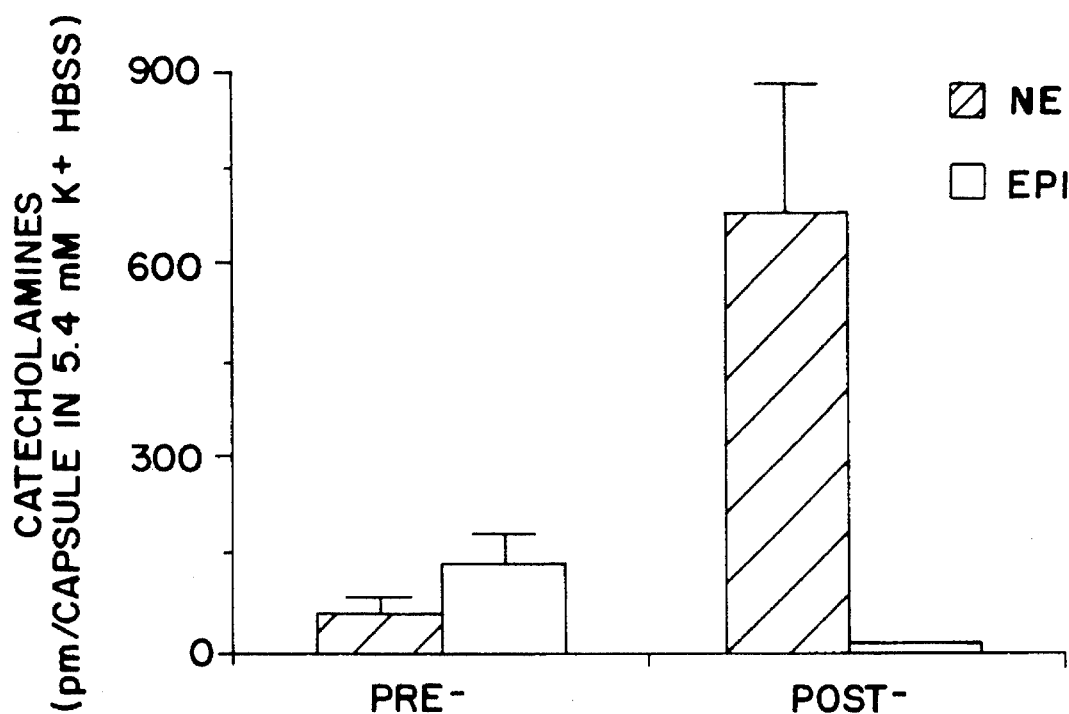
FIG. 7 shows basal (A) and nicotine stimulated (B) catecholamine output by encapsulated calf adrenal chromaffin cells prior to implantation and following retrieval after a 6 month implantation period in the spinal subarachnoid space in rats.
Figure 7B:
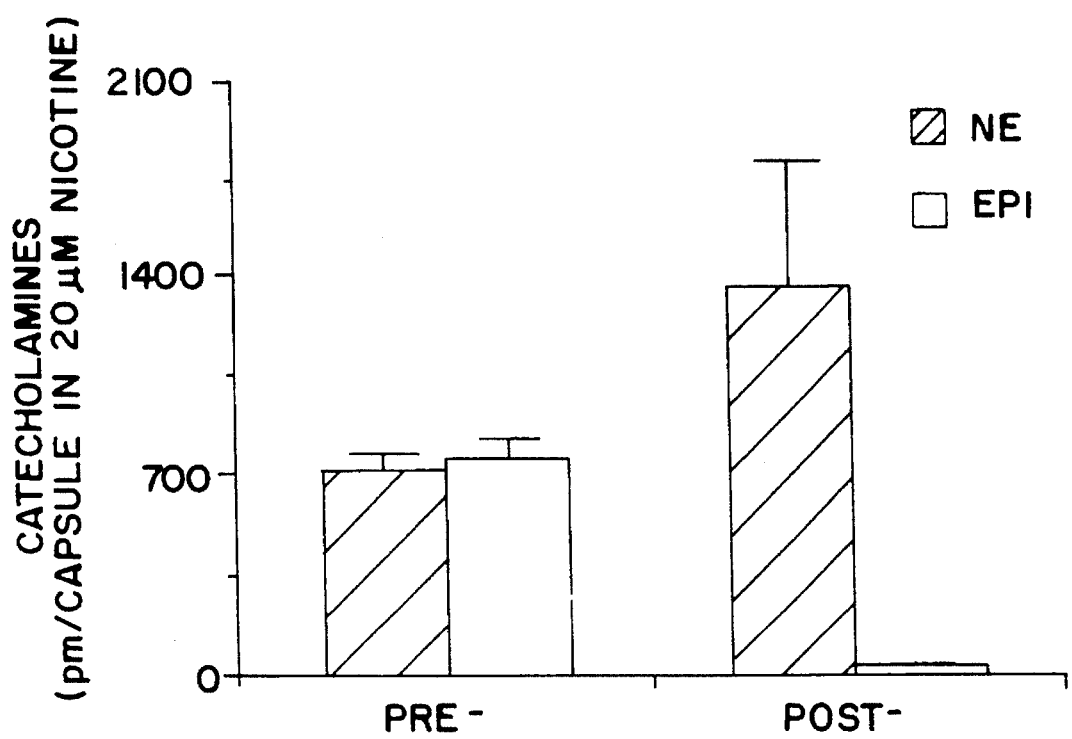
Figure 8A:
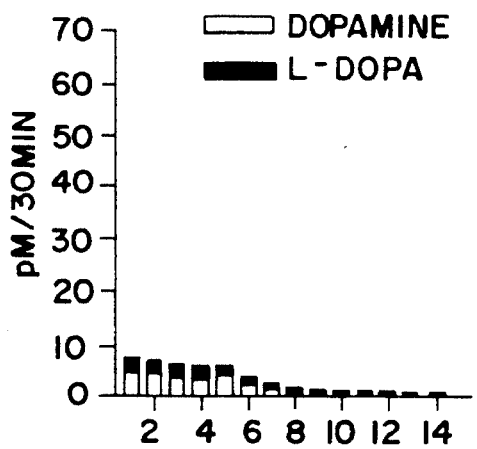
FIG. 8 shows release of dopamine and L-dopa by encapsulated PC12 and PC12A cells prior to implantation and following retrieval after a 3 month implantation period in rat striatum. Panels A and B show pre-implant basal output for PC12 and PC12A cells, respectively. Panels C and D show post-explant basal output for PC12 and PC12A cells, respectively.
Figure 8B:
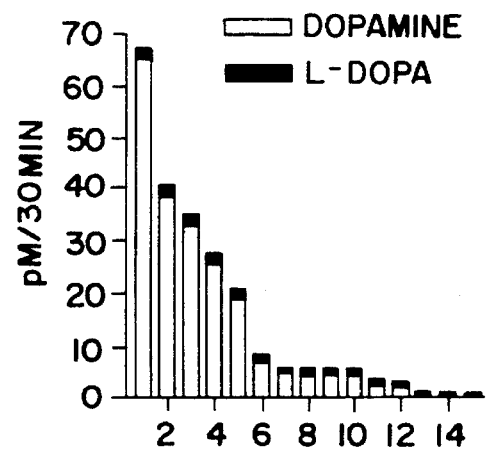
Figure 8C:
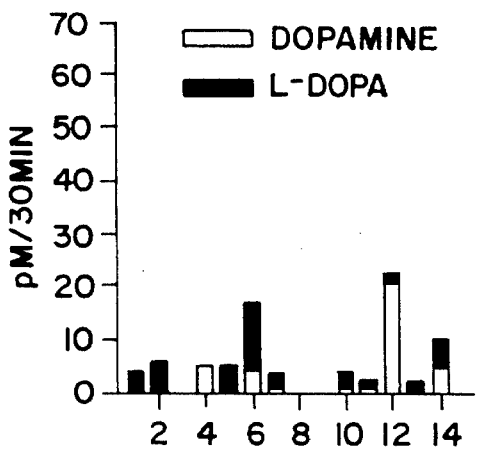
Figure 8D:
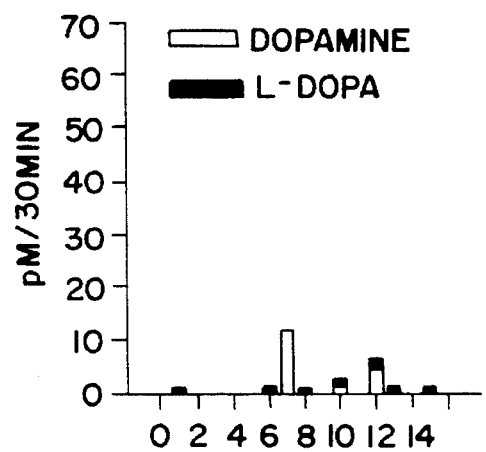

FIG. 7 shows the difference in pre- and post-implantation levels of NE and EPI production. The encapsulated cells were implanted for a period of 6 months. After 6 months in vivo basal and nicotine stimulated, EPI production was significantly decreased, while NE production was significantly increased.

EXAMPLE 7: Encapsulated PC12 cells exposed to in vivo restrictive conditions in primate brain.

PC12 cells were grown in suspension culture in RPMI supplemented with 10% heat inactivated horse serum, 5% fetal calf serum and 100 units penicillin/streptomycin, harvested, centifuged and the supernatant discarded.

Fluka High MW chitosan (4.4 g) was dissolved in 150 ml of sterile 0.85% saline at 70° C., using vigorous stirring. The pH of the solution was adjusted to 6.2 using 45 ml of 100 mM HEPES buffered saline (pH 8.0). The solution was sterile filtered through a 0.22 µm millipore filter.

The chitosan solution was mixed with an equal volume of RPMI and used to resuspend the cell pellet to a concentration of $5\times10^6$ cells/ml. The cells/chitosan solution (approx. 1,000 µl) was coextruded with PAN/PVC, to form single skinned, XP11 immunoisolatory PAN/PVC hollow fiber membranes (ID 450–500 µm, wall 50–65 µm, MWCO 65–100 kD, hydraulic permeability 53 ml/min/m²/mmHg, glucose mass transfer coefficient $8\times10^{-4}$ cm/s, pore size permeability 88% BSA rejection coefficient). These fibers were formed using the general procedure described in U.S. Pat. Nos. 5,158,881, 5,283,187 and 5,284,761. Fibers were trimmed to appropriate dimensions (approx. 1 cm) and sealed by heat crimping the ends.

Encapsulated cells were implanted in three cynomologous monkeys. Surgical procedures were performed substantially as described in Aebischer et al., WO 93/00127. Two capsules were implanted at different positions in the caudate and three capsules implanted at different locations in the putamen. The nominal stereotaxic coordinates for implantation into the putamen and caudate were derived as follows: putamen site 1=23.0 mm anterior from intra-aural zero, 9.0 mm lateral from the sagittal suture and 16.5 mm ventral from the surface of the brain; putamen site 2=19.0 mm anterior from intra-aural zero, 10.0 mm lateral from the sagittal suture and 19.5 mm ventral from the surface of the brain; putamen site 3=15.5 mm anterior from intra-aural zero, 11.5 mm lateral from the sagittal suture and 21.0 mm ventral from the surface of the brain; caudate site 1=18.0 mm anterior from intra-aural zero, 4.0 mm lateral from the sagittal suture and 15.0 mm ventral from the surface of the brain; caudate site 2=22.0 mm anterior from intra-aural zero, 4.5 mm lateral from the sagittal suture and 18.0 mm ventral from the surface of the brain.

The encapsulated cells were implanted for approximately 6 months, and then retrieved. The capsules were assayed for pre and post-implant basal and $K^+$-evoked levels of L-dopa (L-d), norepinephrine (NE), epinephrine (EPI), dopac (dpc), dopamine (DA), and-homovanillic acid (HVA), as described in Example 4. The data shown in Table 2 are expressed as picomoles per capsule per 30 minutes (basal) or picomoles per capsule per 15 minutes ($K^+$-evoked). As the results in Table 2 show, the properties of the encapsulated cells are significantly different after the 6 month exposure to the restrictive conditions.

TABLE 2

| Implant Date | Site | | Basal Levels | | | | | | Potassium Evoked Levels | | | | | |
|---|---|---|---|---|---|---|---|---|---|---|---|---|---|---|
| | | | B L-d | B NE | B EPI | B dpc | B DA | B HVA | K L-d | K NE | K EPI | K dpc | K DA | K HVA |
| 8/9 | C1 | Pre | 1.72 | 1.22 | 1.3 | 3.64 | 10.85 | 3.68 | 0.695 | 2.95 | 1.22 | 3.99 | 23.33 | 2.87 |
| | | Post | 24.2 | 0.65 | 0.3 | 11.9 | 2.995 | 14.7 | 8.796 | 4.63 | nd | 8.07 | 19.44 | 4.67 |
| | C2 | Pre | 2.25 | 3.36 | 3.02 | 8.14 | 32.19 | 10.3 | 0.595 | 5.87 | 2.41 | 7.26 | 46.82 | 5.48 |
| | | Post | 4.22 | nd | 0.32 | 0.42 | nd | 1.11 | 2.08 | nd | nd | nd | 0.826 | nd |
| | P1 | Pre | 1.6 | nd | 0.78 | 0.77 | nd | nd | 0.435 | 0.58 | 0.6 | 1.1 | 3.743 | 0.61 |
| | | Post | 12.1 | 0.85 | 0.18 | 6.06 | 1.664 | 6.3 | 1.358 | 6.35 | nd | 4.29 | 26.18 | 4.34 |
| | P2 | Pre | 1.49 | nd | 0.92 | 1.49 | 0.677 | 1.46 | 0.479 | 0.97 | 0.73 | 1.33 | 7.442 | 1.22 |
| | | Post | 31.8 | 0.54 | nd | 14.5 | 3.679 | 10.2 | 3.599 | 8.4 | nd | 9.47 | 61.11 | 4.39 |
| | P3 | Pre | 1.37 | 0.84 | 0.85 | 2.33 | 8.212 | 2.71 | 0.53 | 1.75 | 0.61 | 1.97 | 13.73 | 1.54 |
| | | Post | 10.8 | 0.72 | nd | 7.13 | 2.448 | 6.01 | 4.681 | 10.6 | nd | 6.73 | 29.65 | 3.65 |
| | Average Pre | | 1.68 | 1.81 | 1.37 | 3.27 | 12.98 | 4.53 | 0.55 | 2.42 | 1.11 | 3.13 | 19 | 2.34 |
| | SD Pre | | 0.34 | 1.36 | 0.94 | 2.92 | 13.51 | 3.94 | 0.1 | 2.13 | 0.77 | 2.58 | 17.2 | 1.94 |
| | Average Post | | 16.6 | 0.55 | 0.26 | 8 | 2.707 | 7.67 | 4.1 | 7.5 | #### | 7.14 | 27.8 | 4.26 |
| | SD Post | | 11.1 | 0.13 | 0.08 | 5.46 | 0.849 | 5.1 | 2.93 | 2.58 | #### | 2.2 | 21.9 | 0.43 |
| 8/10 | C1 | Pre | 1.17 | nd | 0.57 | 0.84 | nd | 0.7 | 0.499 | 0.22 | 0.86 | 0.65 | 1.516 | 0.6 |
| | | Post | 16.6 | 11.9 | 0.91 | 15.4 | 10.13 | 17.2 | 3.533 | 89.2 | nd | 11.1 | 62.63 | 7.08 |
| | C2 | Pre | 1.45 | nd | 0.69 | 0.62 | nd | 0.79 | 0.307 | 0.29 | 0.67 | 0.56 | 1.515 | 0.42 |
| | | Post | 49.9 | 1.34 | nd | 82.6 | 17.55 | 57.4 | 7.49 | 16.1 | nd | 28.9 | 128.7 | 14.1 |
| | P1 | Pre | 1.76 | 1.14 | 1.15 | 3.87 | 10.56 | 3.55 | 0.541 | 3.33 | 1.01 | 3.66 | 22.31 | 2.4 |
| | | Post | 50.4 | 4.04 | 0.41 | 46.2 | 7.45 | 28.6 | 12.02 | 34.8 | nd | 21.6 | 100.7 | 10.8 |
| | P2 | Pre | 1.46 | 0.95 | 0.94 | 2.75 | 9.915 | 2.72 | 0.401 | 1.68 | 0.66 | 2.21 | 11.75 | 1.6 |
| | | Post | 46.8 | 4.09 | nd | 50.8 | 9.309 | 39.1 | 7.639 | 63.7 | nd | 24 | 105.4 | 13.2 |
| | P3 | Pre | 1.49 | nd | 0.87 | 1.83 | nd | 1.95 | 0.531 | 1.08 | 0.79 | 1.71 | 5.59 | 1.33 |
| | | Post | 17.2 | 2.67 | nd | 15 | 6.357 | 17.1 | 5.389 | 24.3 | nd | 5.6 | 41.94 | 3.66 |
| | Average Pre | | 1.46 | 1.05 | 0.84 | 1.98 | 10.24 | 1.94 | 0.46 | 1.32 | 0.84 | 1.76 | 8.53 | 1.27 |
| | SD Pre | | 0.21 | 0.14 | 0.22 | 1.35 | 0.459 | 1.23 | 0.1 | 1.28 | 0.12 | 1.27 | 8.76 | 0.8 |
| | Average Post | | 36.2 | 4.81 | 0.66 | 42 | 10.16 | 31.9 | 7.21 | 45.6 | #### | 18.2 | 87.9 | 9.79 |
| | SD Post | | 17.7 | 4.13 | 0.35 | 28.2 | 4.391 | 16.9 | 3.17 | 30.3 | #### | 9.58 | 35 | 4.38 |
| 8/9 | C1 | Pre | 1.6 | 0.9 | 1.4 | 2.5 | 7 | 2.1 | 0.385 | 1.48 | 0.85 | 1.65 | 11.29 | 1.09 |
| | | Post | 1.5 | nd | 0.22 | 0.27 | 0.827 | 2.91 | 0.906 | nd | nd | nd | 1.789 | nd |
| | C2 | Pre | 1.7 | 1.91 | 1.25 | 4.27 | 17.92 | 3.97 | 0.577 | 3.41 | 1 | 3.86 | 26.13 | 2.24 |
| | | Post | nd | nd | 0.02 | nd | nd | nd | nd | nd | nd | nd | nd | 0.87 |
| | P1 | Pre | 1.38 | 0.14 | 0.85 | 2.93 | 2.284 | 3.02 | 0.367 | 2.68 | 1.12 | 2.45 | 16.9 | 2.35 |
| | | Post | nd | nd | 0.83 | 0.21 | nd | nd | 0.16 | nd | nd | nd | 0.87 | nd |
| | P2 | Pre | 1.66 | nd | 0.68 | 1.08 | 0.489 | nd | 0.489 | 0.96 | 0.5 | 0.86 | 4.856 | nd |

TABLE 2-continued

| Implant Date | Site | \multicolumn{6}{c}{Basal Levels} | | | | | | \multicolumn{6}{c}{Potassium Evoked Levels} | | | | | |
|---|---|---|---|---|---|---|---|---|---|---|---|---|---|
| | | B L-d | B NE | B EPI | B dpc | B DA | B HVA | K L-d | K NE | K EPI | K dpc | K DA | K HVA |
| | Post | nd | nd | 0.05 | nd | nd | 1.72 | nd | nd | nd | nd | nd | nd |
| P3 | Pre | 5.8 | 11.1 | 9.8 | 25.5 | 42 | 19.1 | 1.193 | 8.7 | 5.56 | 16.8 | 66.43 | 7.1 |
| | Post | nd | nd | nd | nd | 1 | 1.9 | 0.13 | nd | nd | nd | nd | nd |
| | Average Pre | 2.47 | 3.51 | 2.8 | 7.26 | 13.94 | 7.05 | 0.6 | 3.45 | 1.81 | 5.12 | 25.1 | 3.2 |
| | SD Pre | 1.87 | 6.11 | 3.93 | 10.3 | 17.09 | 8.07 | 0.34 | 3.09 | 2.11 | 6.62 | 24.4 | 2.66 |
| | Average Post | 1.5 | #### | 0.28 | 0.24 | 0.914 | 2.18 | 0.4 | #### | #### | #### | 1.33 | 0.87 |
| | SD Post | #### | #### | 0.38 | 0.05 | 0.122 | 0.64 | 0.44 | #### | #### | #### | 0.65 | #### |

L-d = L-dopa
NE = norepinephrine
EPI = epinephrine
dpc = dopac
DA = dopamine
HVA = homovanillic acid
C1, C2 = caudate sites
P1, P2, P3 = putamen
nd = not detected EXAMPLE 8: Encapsulated PC12 cells are implanted into a human PC12 cells are encapsulated and implanted in a recipient as described in Example 7. After 6 months, the capsules are explanted and assayed for the l-dopa to dopamine ratio. The cells are plated in multiwell dishes, and cultured under a range of $O_2$ conditions in vitro. The cells are assayed periodically for L-dopa and dopamine output. Cells which release the target L-dopa to dopamine ratio are selected and implanted into human brain, using surgical procedures substantially as described in WO 92/00127.

EXAMPLE 9: Encapsulated PC12 cells exposed to in vivo restrictive conditions in rat striatum.

Capsules

Capsules were prepared from hollow fibers with a phase inversion technique using PAN/PVC hollow fibers substantially as described in Example 7 (ID 450–500 μm, wall 50–65 μm, mMWCO 100 kD, hydraulic permeability 53 ml/min/m$^2$/mmHg).

Cell Culture and Encapsulation

PC12 and PC12A cells were cultivated in 500 ml spinner cultures at 80 RPM in a serum-free defined medium HL-1 (Ventrex, Inc., Portland, Me.) at 37° C. in a water-saturated, 7% $CO_2$ ambiant air atmosphere. Cells were harvested by collecting spinner culture supernatant and centrifugating at 800 g. Viability was assessed by exclusion of trypan blue and shown to be 90±5% prior to encapsulation.

The cells were resuspended in HL-1, pH 7.3, at a concentration of $4 \times 10^7$ cells/ml. An equal volume of a solution containing 2% (w/v) of pH 6.7 low viscosity chitosan (PROTOSAN®, chitosan chloride, Protan Biopolymer, Drammen, Norway), was added to the PC12 and PC12A cells resulting in a final cell concentration of $2.0 \times 10^7$ cells/ml.

Individual capsules were 7±0.5 mm in length. PC12 and PC12A cell-loaded capsules were fabricated in two separate batches and placed in a 24 multiwell tissue culture plate containing 1 ml of HL-1 medium.

At 5–7 days following encapsulation, free-floating capsules were washed twice with 1 mL of HBSS HEPES buffered saline (containing 10 μM ascorbate) to remove residual culture medium. Sampling consisted of a 30 min incubation (basal release) in 250 μL HBSS. All samples were protected from oxidation by the rapid addition of a citrate-reducing acidified buffer (CRAB) and yielded a stable sample preparation in 10 mM citric acid, 20 μM sodium metabisulfite, and 0.1 N perchloric acid. Extended storage was at −80° C. Standards were prepared by diluting stock solutions into HBSS and stabilizing them with CRAB and 0.1 N perchloric acid.

Striatal Dopamine Depletions

Rats were anesthetized with a 1.0 ml/kg intramuscular injection of a mixture of ketamine (33 mg/ml), xylazine (1.7 mg/ml), and acepromazine (10 mg/ml) and positioned in a Kopf stereotaxic instrument. A total of 12 μg of 6-OHDA (6 μl volume at a concentration of 2 μg/μl dissolved in 0.9% saline containing 0.2 μg/μl ascorbic acid) were infused at a rate of 1.0 μl/minute and allowed to diffuse for 5 minutes before the infusion cannula was slowly retracted. Infusion coordinates were 4.2 mm posterior to bregma, 1.0 mm lateral from midline, and 7.4 mm ventral to dura.

Capsule Implantation

Four months after being lesioned (2.75 months after the last apomorphine injection), capsules were implanted. Rats were anesthetized as before, and a sagittal incision was made in the scalp and a hole drilled for placement of the polymer capsule. Rats were implanted by placing the capsule within an 18-gauge Teflon catheter mounted to the stereotaxic frame. A stainless steel obturator was placed within the cannula, the device lowered into the brain, and the obdurator held in place while the outer cannula was raised to passively place the capsule within the host striatum. The stereotaxic coordinates for implantation were: 0.5 mm anterior to bregma, 3.8 mm lateral to the sagittal suture, and 7.5 mm below the surface of the cortex. Rats not receiving implants were given sham surgeries (anesthetized, scalp lacerated, skull drilled, and dura punctured).

Biochemical Analysis

After the completion of behavioral testing, rats with no capsules, PC12, PC12A, and half the rats with the empty capsules were anesthetized in a $CO_2$ chamber and quickly decapitated. Their brains were removed from the skulls, the capsules were removed, both striata were dissected out, placed in Eppendorf tubes, and quick-frozen in liquid nitrogen. Following capsule retrieval from the host striatum, capsules were placed in 1 ml of phosphate HBSS for approximately 30 min. The phosphate HBSS was removed, and 1 ml of HEPES HBSS was added. Catecholamine analyses were performed as described in Example 4. After the catecholamine assay was completed the devices were placed in 4% paraformaldehyde and submitted for morphologic analyses.

FIG. 8 shows release of dopamine and L-dopa measured over a 30 minute period plotted for individual capsules, each assigned an identifier number. As shown in FIG. 8, the 90 day post-implant production levels Of L-dopa and dopamine were significantly different than the pre-implant levels.

EXAMPLE 10: Encapsulated adrenal chromaffin cells exposed to in vivo restrictive conditions in the human subarachnoid space Bovine adrenal chromaffin cells were prepared as described in Example 4. Adrenal cell aggregates were immobilized in a 1.5% alginate matrix crosslinked with $CaCl_2$ and encapsulated in double skinned Type 4, immunoisolatory PAN/PVC hollow fiber membranes (ID 770 μm, wall 70 μm, MWCO 60–100 kD), substantially as described in WO92/19195.

The encapsulated cells were implanted in the subarachnoid space in two human patients, with terminal cancer, pain incompletely relieved by narcotic therapy, and no evidence of active infection or tumor in the meningeal space. Informed consent was granted by the patients and approval was received from the Ethical Committee of the Faculty of Medicine of the University of Lausanne, Switzerland.

Local infiltration with 1.0% lidocaine was used to establish anesthesia of the skin as well as the periosteum and other deep connective tissue structures down to and including the ligamentum flavum. A 3–5 cm skin incision was made in the parasagital plane 1–2 cm to the right or left of the midline and was continued down to the lumbodorsal fascia. Using traditional bony landmarks including the iliac crests and the lumbar spinous processes, as well as fluoroscopic guidance, an 18 gauge Touhy needle was introduced into the subarachnoid space between L-3 and L-4 via an oblique paramedian approach. The needle was directed so that it entered the space at a shallow, superiorly directed angle that was no greater than 30°–35° with respect to the spinal cord in either the sagittal or transverse plane.

A guide wire was passed down the lumen of the Touhy needle hub until it extended 4–5 cm into the subarachnoid space (determined by premeasuring). The Touhy needle was removed from the wire.

A 7 French dilator was then placed over the guide wire and the wire was used to direct the dilator as it was gently but firmly pushed through the fascia, paraspinous muscle, and ligamentum flavum, following the track of the wire toward the subarachnoid space.

After the wire track was "overdilated" by the 7 French dilator, a 6 French dilator and cannula sheath were assembled and placed over the guide wire. The 6 French dilator and cannula were advanced carefully into the subarachnoid space until the opening tip of the cannula was positioned 7 cm within the space.

When appropriate positioning of the cannula was assured, the guide wire and the 6 French dilator were gently removed from the lumen of the cannula in sequence.

The encapsulated adrenal chromaffin cell was provided in a sterile, double envelope container, bathed in transport medium, and fully assembled including a tubular silicone tether. The membrane portion of the device was carefully introduced into the cannula. The capsule was advanced until the tip of the membrane reached a point that was 2–10 mm within the cranial tip of the cannula in the subarachnoid space. After the capsule was positioned using a pusher, the cannula and pusher were completely withdrawn. The final placement of the capsule was such that the 5 cm long membrane portion of the device lay entirely within the CSF containing subarachnoid space ventral to the cauda equina.

The capsules were explanted after 84 days in patient 1 and after 55 days in patient 2. Catecholamine output—norepinephrine ("NE") and epinephrine ("EPI")—after the exposure to in vivo restrictive conditions was compared with pre-implant levels (Table 3). Catecholamines were measured as described in example 4. The data in Table 3 are expressed as picomoles per capsule per 30 min (Basal) or picomoles per capsule per 15 min (nicotine stimulated: N-S). The catecholamine output was significantly different after exposure to the restrictive conditions than before implantation.

TABLE 3

| | Capsule Catecholamine Output | | | |
|---|---|---|---|---|
| | implant | | explant | |
| | NE | E | NE | E |
| Patient 1: Implantation For 84 Days | | | | |
| Basal | 0 | 84 | 37 | 8 |
| N-S | 2932 | 2673 | 6366 | 3886 |
| Patient 2: Implantation For 55 Days | | | | |
| Basal | 48 | 120 | 4.1 | 69.3 |
| N-S | 5027 | 5063 | 10.6 | 65 |

We claim:

1. A method for preparing encapsulated cells for implanting at an implantation site in a human comprising the steps of:

(a) encapsulating the cells in a biocompatible capsule, and (b) exposing the cells to at least one restrictive condition that closely matches a condition at the implantation site and which establishes a measurable change in at least one cell property in response to the restrictive condition.

2. The method of claim 1 wherein the encapsulated cells are exposed to the restrictive condition in vitro.

3. The method of claim 1 wherein the encapsulated cells are exposed to the restrictive condition in vivo by implantation at an implantation site in a recipient prior to implantation at an implantation site in a human.

4. The method of claim 1 wherein the cells are xenogeneic to the host and the capsule is immunoisolatory.

5. The method of claim 1 wherein at least one restrictive condition is a glucose concentration ranging from about 40 mg/deciliter to about 70 mg/deciliter.

6. The method of claim 1 wherein at least one restrictive condition is an oxygen concentration ranging from about 40 mmHg to about 65 mmHg.

7. The method of claim 3 wherein the cells are selected from the group consisting of adrenal chromaffin cells, baby hamster kidney cells, and PC12 cells.

8. The method of claim 7 wherein the cells are adrenal chromaffin cells and are implanted in a recipient for 4 months or longer.

9. The method of claim 7 wherein the cells are PC12 cells and are implanted in a recipient for 6 months or longer.

10. The method of claim 1 wherein the cells produce a biologically active molecule selected from the group consisting of neurotransmitters, analgesics and growth factors.

11. The method of claim 1 wherein the capsule is implanted in a host at an implantation site selected from the group consisting of cerebrospinal fluid or brain parenchyma.

12. The method of claim 1 wherein the host is a human.

13. A method for preparing encapsulated cells for implanting at an implantation site in a xenogeneic host comprising the steps of:

(a) culturing the cells under at least two restrictive conditions, and (b) encapsulating the cells in a biocompatible capsule and further exposing the encapsulated cells to at least one restrictive condition that closely matches a condition at the implantation site and which establishes a measurable change in at least one cell property in response to the restrictive condition.

* * * * *